US007417136B1

(12) United States Patent
Chang

(10) Patent No.: US 7,417,136 B1
(45) Date of Patent: Aug. 26, 2008

(54) NUCLEIC ACID *VACCINES* FOR PREVENTION OF FLAVIVIRUS INFECTION

(75) Inventor: Gwong-Jen J. Chang, Fort Collins, CO (US)

(73) Assignee: The United States of America as represented by the Secretary, Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 09/701,536

(22) PCT Filed: Jun. 3, 1999

(86) PCT No.: PCT/US99/12298

§ 371 (c)(1),
(2), (4) Date: Jun. 18, 2001

(87) PCT Pub. No.: WO99/63095

PCT Pub. Date: Dec. 9, 1999

Related U.S. Application Data

(60) Provisional application No. 60/087,908, filed on Jun. 4, 1998.

(51) Int. Cl.
*C07H 21/04* (2006.01)
*A61K 39/12* (2006.01)

(52) U.S. Cl. ................................ 536/23.72; 424/218.1

(58) Field of Classification Search ............. 424/218.1; 536/23.72, 24.1
See application file for complete search history.

(56) References Cited

U.S. PATENT DOCUMENTS

| | | | | |
|---|---|---|---|---|
| 4,810,492 | A | 3/1989 | Fujita et al. | |
| 5,021,347 | A | 6/1991 | Yasui et al. | |
| 5,229,293 | A | 7/1993 | Matsuura et al. | |
| 5,494,671 | A | 2/1996 | Lai et al. | |
| 5,514,375 | A | 5/1996 | Paoletti et al. | |
| 6,074,865 | A | 6/2000 | Kelly et al. | |
| 6,136,561 | A | 10/2000 | Ivy et al. | |
| 6,165,477 | A | 12/2000 | Ivy et al. | |
| 6,258,788 | B1 * | 7/2001 | Schmaljohn | 514/44 |
| 6,455,509 | B1 * | 9/2002 | Kochel et al. | 514/44 |

FOREIGN PATENT DOCUMENTS

| | | |
|---|---|---|
| JP | 53133627 | 11/1978 |
| JP | 63004895 | 1/1988 |
| JP | 63105682 | 5/1988 |
| JP | 89025725 | 5/1989 |
| JP | 65000611 | 1/1990 |
| JP | 67025408 | 1/1992 |
| JP | 7265093 | 10/1995 |
| WO | WO 90/01946 | 3/1990 |
| WO | WO 92/02548 | 2/1992 |
| WO | WO 92/03545 | 3/1992 |
| WO | WO 93/06214 | 4/1993 |
| WO | WO 98/37911 | 9/1998 |
| WO | WO 99/06068 | 2/1999 |
| WO | WO 99/63095 | 12/1999 |
| WO | WO 02/072036 | 9/2002 |

OTHER PUBLICATIONS

Phillpotts, R. J., et al., 1996, Immunisation with DNA polynucleotides protects mice against lethal challenge with St. Louis encephalitis virus, Arch. Virol. 141:743-749.*

Kozak, M., 1987, At least six nucleotides preceding the AUG initiation condon enhance translation in mammalian cells, J. Mol. Biol. 196:947-950.*

Konishi, E., et al., 1992, Mice immunized with a subviral particle containing the Japanese encephalitis virus prM/M and E proteins are protected from lethal JEV infection, Virol. 188:714-720.*

Aberle et al. "A DNA Immunization Model Study with Constructs Expressing the Tick-Borne Encephalitis Virus Envelope Protein E in Different Physical Forms" *J Immunology* 163: 6756-6761, 1999.

Konishi et al. "Induction of Protective Immunity against Japanese Encephalitis in Mice by Immunization with a Plasmid Encoding Japanese Encephalitis Virus Premembrane and Envelope Genes" *J Virology* 72(6): 4925-4930, Jun. 1998.

Lin et al. "DNA Immunization with Japanese Encephalitis Virus Nonstructural Protein NS1 Elicitis Protective Immunity in Mice" *J Virology* 72(1): 191-200, Jan. 1998.

Ho et al. "DNA vaccination induces a long-term antibody response and protective immunity against pseudorabies virus in mice" *Arch Virol* 143: 115-125, 1998.

Kochel et al. "Inoculation of plasmids expressing the dengue-2 envelope gene elicit neutralizing antibodies in mice" *Vaccine* 15(5): 547-552, 1997.

Wang et al. "Immune Response to Neonatal Genetic Immunization" *Virology* 288: 278-284, 1997.

Phillpotts et al. "Immunization with DNA polynucleotides protects mice against lethal challenge with St. Louis encephalitis virus" *Arch Virol* 141: 743-749, 1996.

(Continued)

*Primary Examiner*—Jeffrey S. Parkin
(74) *Attorney, Agent, or Firm*—Klarquist Sparkman, LLP

(57) ABSTRACT

The invention encompasses nucleic acid molecules containing transcription units which encode the flavivirus M and E protein antigens. The *flaviviruses* include *Japanese encephalitis virus, dengue, yellow fever virus* and *St. Louis encephalitis virus*. The nucleic acids function to provide the M and E protein antigens when the nucleic acid resides in an appropriate host cell, especially when the host cell is the cell of a subject. The invention also encompasses a vaccine whose active agent is the nucleic acid. The invention further encompasses the cultured host cells when they contain within them nucleic acid molecules containing the transcription units. The invention in addition encompasses a method of immunizing a subject against flavivirus infection by administering to the subject an effective amount of a vaccine containing a nucleic acid molecule containing the transcription unit of the invention.

21 Claims, 8 Drawing Sheets

OTHER PUBLICATIONS

Venugopal et al. "Immunity to St. Louis encephalitis virus by sequential immunization with recombinant vaccinia and baculovirus derived PrM/E proteins" *Vaccine* 13(11): 1000-1005, 1995.
Allison et al. "Synthesis and Secretion of Recombinant Tick-Borne Encephalitis Virus Protein E in Soluble and Particulate Form" *J Virology* 69(9): 5816-5820, Sep. 1995.
Abstract, Japanese Patent Publication No. JP 5276941 "Non-infective structure particle preparation, useful as vaccine—by infecting preliminary flavivirus infected cell with cDNA integrated recombinant vaccinia virus, and then separating non-infective structure particles containing E protein of flavivirus" Oct. 26, 1993.
Wolff et al. "Long-term persistence of plasmid DNA and foreign gene expression in mouse muscle" Hum Mol Genet 1(6): 363-369, Sep. 1992.
Konishi et al. "Mice Immunized with a Subviral Particle Containing the Japanese Encephalitis Virus prM/M and E Proteins Are Protected from Lethal JEV Infection" *Virology* 188: 714-720, 1992.
Mason et al. "Japanese Encephalitis Virus-Vaccinia Recombinants Produce Particulate Forms of the Structural Membrane Proteins and Induce High Levels of Protection against Lethal JEV Infection" *Virology* 180: 294-305, 1991.
Osatomi and Sumiyoshi "Complete Nucleotide Sequence of Dengue Type 3 Virus Genome RNA" *Virology* 176: 643-647, 1990.
Seeger et al. "The cloned genome of ground squirrel hepatitis virus is infectious in the animal" *Proc Natl Acad Sci* U.S.A 81(18): 5849-5852, Sep. 1984.
Alvarez et al. A Phase I Study of Recombinant Adenovirus Vector-Mediated Delivery of an Anti-erbB-2 Single-Chain (sFv) Antibody Gene for Previously Treated Ovarian and Extraovarian Cancer Patients. *Hum. Gene Ther.* 8:229-242 (Jan. 20, 1997).
Selay. The Choice Carrier. *Synthetic Vaccines* vol. I (edited by Arnon) CRC Press Inc., Boca Raton, FL. pp. 83-92 (1987).
Clarke et al. Techniques For Hemagglutination And Hemagglutination-Inhibition With Arthropod-Borne Viruses. *Amer. J. Trop. Med. and Hyg.* 7:561-573 (1958).
Gruenberg et al. Partial Nucleotide Sequence and Deduced Amino Acid Sequence of the Structural Proteins of Dengue Virus Type 2, New Guinea C and PUO-218 Strains. *J. Gen. Virol.* 69:1391-1398 (1988).
Henchal et al. Dengue Virus-Specific And Flavivirus Group Determinants Identified With Monoclonal Antibodies By Indirect Immunofluorescence. *Amer. J. Trop. Med. Hyg.* 31:830-836 (1982).
Hubálek et al. West Nile Fever-a Reemerging Mosquito-Borne Viral Disease in Europe. *Emerg. Infect. Dis.* 5(5):643-650 (1999).
Kohler et al. Continuous cultures of fused cells secreting antibody of predefined specificity. *Nature* 256:495-497 (Aug. 7, 1975).
Konishi et al. Avipox virus-vectored Japanese encephalitis virus vaccines: use as vaccine candidates in combination with purified subunit immunogens. *Vaccine* 12(7):633-638 (1994).
Kozak. Circumstances and Mechanisms of Inhibition of Translation by Secondary Structure in Eucaryotic mRNAs. *Mol. Cell. Biol.* 9(11):5134-5142 (Nov. 1989).
Laemmli. Cleavage of Structural Proteins during the Assembly of the Head of Bacteriophage T4. *Nature* 277:680-685 (Aug. 15, 1970).
Lai et al. Immunization of Monkeys with Baculovirus Recombinant-expressed Dengue Envelope and NS1 Glycoproteins Induces Partial Resistance to Challenge with Homotypic Dengue Virus. In *Vaccines 90: Modern Approaches to New Vaccines including Prevention of AIDS*, Cold Spring Harbor Laboratory, Cold Springs Harbor, NY pp. 119-124 (1990).
Mason et al. Sequence of the Dengue-1 Virus genome in the Region Encoding the Three Structural Proteins and the Major Nonstructural Protein NS1. *Virology* 161:262-267 (1987).
Smithburn et al. A Neurotropic Virus Isolated From The Blood Of A Native Of Uganda. *Am. J. Trop. Med. Hyg.* 20:471-492 (1940).
Tardei et al. Evaluation of Immunoglobulin M (IgM) and IgG Enzyme Immunoassays in Serologic Diagnosis of West Nile Virus Infection. *J. Clin. Microbiol.* 38(6):2232-2239 (Jun. 2000).
Tsai et al. Japanese Encephalitis Vaccines. In *Vaccines* ($3^{rd}$ edition) (edited by Plotkin and Orenstein), W.B. Saunders Co., Philadelphia, PA. Chapter 27, pp. 672-710 (1999).
Tsai et al. Japanese Encephalitis Vaccines. In *Vaccines* (2nd edition) (edited by Plotkin and Mortimer), W.B. Saunders Co., Philadelphia, PA. Chapter 24, pp. 671-713 (1994).
Yang et al. A p300/CBP-associated factor that competes with the adenoviral oncoprotein E1A. *Nature* 382:319-324 (Jul. 25, 1996).
Anderson et al., "Isolation of West Nile Virus from Mosquitoes, Crows, and a Cooper's Hawk in Connecticut," *Science* 286(5448):2331-2333, Dec. 17, 1999.
Asnis et al., "The West Nile Virus Outbreak of 1999 in New York: The Flushing Hospital Experience," *Clin. Infect. Dis.* 30:413-418, 2000.
Azevedo et al., "Main features of DNA-based immunization vectors," *Braz. J. Med. Biol. Res.* 32(2):147-153, 1999.
Bray et al., "Mice Immunized with Recombinant Vaccinia Virus Expressing Dengue 4 Virus Structural Proteins with or without Nonstructural Protein NSI Are Protected Against Fatal Dengue Virus Encephalitis," *J. Virol.* 63(6):2853-2856, Jun. 1989.
Chang et al., "A Single Intramuscular Injection of Recombinant Plasmid DNA Induces Protective Immunity and Prevents Japanese Encephalitis in Mice," *J. Virol.* 74(9):4244-4252, May 2000.
Davis et al., "West Nile Virus Recombinant DNA Vaccine Protects Mouse and Horse from Virus Challenge and Expresses in Vitro a Noninfectious Recombinant Antigen That Can Be Used in Enzyme-Linked Immunosorbent Assays," *J. Virol.* 75(9):4040-4047, 2001 (published on-line Apr. 4, 2001).
Deubel et al., "Nucleotide Sequence and Deduced Amino Acid Sequence of the Structural Proteins of Dengue Type 2 Virus, Jamaica Genotype," *Virology* 155:365-377, 1986.
Deubel et al., "Nucleotide Sequence and Deduced Amino Acid Sequence of the Nonstructural Proteins of Dengue Type 2 Virus, Jamaica Genotype: Comparative Analysis of the Full-Length Genome," *Virology* 165:234-244, 1988.
Duarte dos Santos et al., "Complete nucleotide sequence of yellow fever virus vaccine strains 17DD and 17D-213," *Virus Res.* 35:35-41, 1995.
Falgout et al., "Proper Processing of Dengue Virus Nonstructural Glycoprotein NSI Requires the N-Terminal Hydrophobic Signal Sequence and the Downstream Nonstructural Protein NS2a," *J. Virol.* 63(5):1852-1860, May 1989.
Falgout et al., "Immunization of Mice with Recombinant Vaccinia Virus Expressing Authentic Dengue Virus Nonstructural Protein NSI Protects Against Lethal Dengue Virus Encephalitis," *J. Virol.* 64(9):4356-4363, 1990.
Fonseca et al. "Recombinant vaccinia viruses co-expressing dengue-1 glycoprotein prM and E induce neutralizing antibodies in mice," *Vaccine* 12(3):279-285, 1994.
Mackow et al., "The Nucleotide Sequence of Dengue Type 4 Virus: Analysis of Genes Coding for Nonstructural Proteins," *Virology* 159:217-228, 1987.
Mandl et al., "Complete Genomic Sequence of Powassan Virus: Evaluation of Genetic Elements in Tick-Borne Versus Mosquito-Borne Flaviviruses," *Virology* 194:173-184, 1993.
Martin et al., "Standardization of Immunoglobulin M Capture Enzyme-Linked Immunosorbent Assays for Routine Diagnosis of Arboviral Infections," *J. Clin. Microbiol.* 38(5):1823-1826, May 2000.
Mir et al., "High-efficiency gene transfer into skeletal muscle mediated by electric pulses," *Proc. Nat. Acad. Sci. USA* 96:4262-4267, Apr. 1999.
Monath, "Flaviviruse," *Virology* (R.N. Fields, ed.) 763-814, 1990.
Nitayaphan et al., "Nucleotide Sequence of the Virulent SA-14 Strain of Japanese Encephalitis Virus and Its Attenuated Vaccine Derivative, SA-14-14-2," *Virology* 177:541-552, 1990.
Osatomi et al., "Nucleotide Sequence of Dengue Type 3 Virus Genomic RNA Encoding Viral Structural Proteins," *Virus Genes* 2(1):99-108, 1988.
Pincus et al., "Recombinant vaccinia virus producing the prM and E proteins of yellow fever virus protects mice from lethal yellow fever encephalitis," *Virology* 187:290-297, 1992.
Ramelow et al., "Detection of tick-borne encephalitis virus RNA in ticks (*Ixodes ricinus*) by the polymerase chain reaction," *J. Virol. Meth.* 45:115-9, 1993.

Rice et al., "Nucleotide Sequence of Yellow Fever Virus: Implications for Flavivirus Gene Expression and Evolution," *Science* 229:726-733, Aug. 23, 1985.
Roehrig et al., "Identification of Epitopes on the E Glycoprotein of Saint Louis Encephalitis Virus Using Monoclonal Antibodies," *Virology* 128:118-126, 1983.
Sato et al., "Immunostimulatory DNA Sequences Necessary for Effective Intradermal Gene Immunization," *Science* 273(5273):352-354, Jul. 19, 1996.
Schalich, et al., "Recombinant subviral particles from tick-borne encephalitis virus are fusogenic and provide a model system for studying flavivirus envelope glycoprotein functions," *J. Virol.* 70:4549-4557, Jul. 1996.
Sela The Choice of Carrier. *Synthetic Vaccines Volume I* (edited by Arnon) CRC Press Inc., Boca Raton, FL. pp. 83-92, 1987.
Sumiyoshi et al., "Complete Nucleotide Sequence of the Japanese Encephalitis Virus Genome RNA," *Virology* 161:497-510, 1987.
Trent et al., "Partial Nucleotide Sequence of St. Louis Encephalitis Virus RNA: Structural Proteins. NS1 ns2a and ns2b," *Virology* 156:293-304, 1987.
Zhang et al., "Immunization of Mice with Dengue Structural Proteins and Nonstructural Protein NSI Expressed by Baculovirus Recombinant Induces Resistance to Dengue Virus Encephalitis," *J. Virol.* 62(8):3207-3031, Aug. 1988.
Zhang et al., "Passive Protection of Mice, Goats, and Monkeys Against Japanese Encephalitis With Monoclonal Antibodies," *J. Med. Virol.* 29:133-138, 1989.
Zhao et al., "Cloning full-Length Dengue Type 4 Viral DNA Sequences: Analysis of Genes Coding for Structural Proteins," *Virology* 155:77-88, 1986.
Zhao et al., "Expression of Dengue Virus Structural Proteins and Nonstructural Protein $NS_1$ by a Recombinant Vaccinia Virus," *J. Virol.* 61(12):4019-4022, Dec. 1987.
"Update: Surveillance for West Nile Virus in Overwriting Mosquitos—New York, 2000," *Morb. Mortal. Wkly. Rep.* 49(09):178-179, Mar. 10, 2000.
"Update: West Nile Virus Activity—Northeastern United States, 2000," *Morb. Mortal. Wkly. Rep.* 49(36):820-822, Sep. 15, 2000.
Colombage et al., "DNA-Based and Alphavirus-Vectored Immunisation with PrM and E Proteins Elicits Long-Lived and Protective Immunity against te Flavivirus, Murray Valley Encephalitis Virus," *Virology* 250:151-163, 1998.
Konishi et al., "The Anamnestic Neutralizing Antibody Response Is Critical for Protection of Mice from Challenge following Vaccination with a Plasmid Encoding the Japanese Encephalitis Virus Premembrane and Envelope Genes," *J. Virology* 73(7):5527-5534, Jul. 1999.
Konishi et al., "A DNA vaccine expressing dengue type 2 virus premembrane and envelope genes induces neutralizing antibody and memory B cells in mice," *Vaccine* 18:1133-1139, 2000.
Porter et al., "Protective efficacy of a dengue 2 DNA vaccine in mice and the effect of CpG immuno-stimulatory motifs on antibody responses, " *Arch. Virol.* 143:997-1003, 1998.
Raviprakash et al., "Immunogenicity of dengue virus type 1 DNA vaccines expressing truncated and full length envelope protein," *Vaccine* 18:2426-2434, 2000.
Wang et al., "Immunization of Mice Against West Nile Virus with Recombinant Envelope Protein," *J. Immunol.* 167:5273-5277, 2001.
Chang et al., "Enhancing biosynthesis and secretion of premembrane and envelope proteins by the chimeric plasmid of dengue virus type 2 and Japanese encephalitis virus," *Virology*, 306:170-180, 2003.
Chang et al., "Flavivirus DNA Vaccines," *Annals New York Academy of Sciences*, 272-285.
Hunt et al., "A recombinant particulate antigen of Japanese encephalitis virus produced in stably-transformed cells is an effective noninfectious antigen and submit immunogen," *J. Virological Methods*, 97:133-149, 2001.
Cavener and Ray, "Eukaryotic start and stop translation sites," *Nucleic Acids Research*, 19(12):3185-3192 (1991).
Kozak, "At Least Six Nucleotides Preceding the AUG Initiator Codon Enhance Translation in Mammalian Cells," *J. Mol. Biol.*, 196:947-950 (1987).
Kozak, "Point Mutations Define a Sequence Flanking the AUG Initiator Codon That Modulates Translation by Eukaryotic Ribosomes," *Cell*, 44:283-292 (Jan. 31, 1986).
Chang et al., "Recent advancement in flavivirus vaccine development," *Expert Rev. Vaccines*, 3(2):199-220 (2004).
Guirakhoo et al., "Recombinant Chimeric Yellow Fever-Dengue Type 2 Virus is Immunogenic and Protective in Nonhuman Primates," *J. Virol.*, 74(12):5477-5485 (2000).
Simmons et al., "Short Report: Antibody Responses of Mice Immunized with a Tetravalent Dengue Recombinant Protein Subunit Vaccine," *Am. J. Trop. Med. Hyg.* 65(2):159-161 (2001).
Yasui, et al., "Analysis of Japanese encephalitis (JE) virus genome and implications for recombinant JE vaccine," *Southeast Asian J. Trop. Med. Public Health*, 21(4):663-669. 1990.

* cited by examiner

SEQUENCE LISTING

<160> NUMBER OF SEQ ID NOS: 17

<210> SEQ ID NO 1
<211> LENGTH: 48
<212> TYPE: DNA
<213> ORGANISM: Artificial Sequence
<220> FEATURE:
<223> OTHER INFORMATION: Synthetic sequence -continued

```
<220> FEATURE:
<221> NAME/KEY: CDS
<222> LOCATION: (25)..(48)

<400> SEQUENCE: 1

cttggtacct ctagagccgc cgcc atg ggc aga aag caa aac aaa aga            48
                           Met Gly Arg Lys Gln Asn Lys Arg
                           1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Met Gly Arg Lys Gln Asn Lys Arg
1               5


<210> SEQ ID NO 3
<211> LENGTH: 50
<212> TYPE: DNA
<213> ORGANISM: Artificial Sequence
<220> FEATURE:
<223> OTHER INFORMATION: Synthetic sequence

<400> SEQUENCE: 3

ttttcttttg cggccgctca aacttaagca tgcacattgg tcgctaagaa                50


<210> SEQ ID NO 4
<211> LENGTH: 27
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(27)
<223> OTHER INFORMATION: reverse complement of positions 24-50 of SEQ ID
      NO: 3
<220> FEATURE:
<221> NAME/KEY: CDS
<222> LOCATION: (1)..(27)

<400> SEQUENCE: 4

ttc tta gcg acc aat gtg cat gct taa                                   27
Phe Leu Ala Thr Asn Val His Ala
1               5


<210> SEQ ID NO 5
<211> LENGTH: 8
<212> TYPE: PRT
<213> ORGANISM: Artificial sequence
<220> FEATURE:
<223> OTHER INFORMATION: Synthetic Construct

<400> SEQUENCE: 5

Phe Leu Ala Thr Asn Val His Ala
1               5


<210> SEQ ID NO 6
<211> LENGTH: 7
<212> TYPE: DNA
<213> ORGANISM: Artificial sequence
<220> FEATURE:
<223> OTHER INFORMATION: Part of plasmid

<400> SEQUENCE: 6
```

-continued

```
tatataa                                                                  7


<210> SEQ ID NO 7
<211> LENGTH: 77
<212> TYPE: DNA
<213> ORGANISM: artificial sequence
<220> FEATURE:
<223> OTHER INFORMATION: Multicloning site

<400> SEQUENCE: 7

ggtaccgagc tcggatccag tagtaacggc cgccagtgtg ctggaattct gcagatatcc     60

atcacactgg cggccgc                                                      77


<210> SEQ ID NO 8
<211> LENGTH: 48
<212> TYPE: DNA
<213> ORGANISM: Artificial Sequence
<220> FEATURE:
<223> OTHER INFORMATION: Synthetic sequence
<220> FEATURE:
<221> NAME/KEY: CDS
<222> LOCATION: (25)..(48)

<400> SEQUENCE: 8

cttggtacct ctagagccgc cgcc atg cgt tcc cat gat gtt ctg act            48
                           Met Arg Ser His Asp Val Leu Thr
                           1               5


<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Met Arg Ser His Asp Val Leu Thr
1               5


<210> SEQ ID NO 10
<211> LENGTH: 41
<212> TYPE: DNA
<213> ORGANISM: Artificial Sequence
<220> FEATURE:
<223> OTHER INFORMATION: Synthetic sequence

<400> SEQUENCE: 10

ttttcttttg cggccgctca cgccccaact cctagagaaa c                          41


<210> SEQ ID NO 11
<211> LENGTH: 24
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(24)
<223> OTHER INFORMATION: reverse complement of positions 18 through 41
      of SEQ ID NO: 8
<220> FEATURE:
<221> NAME/KEY: CDS
<222> LOCATION: (1)..(24)

<400> SEQUENCE: 11

ttg tct cta gga gtt ggg gcg tga                                        24
Leu Ser Leu Gly Val Gly Ala
```

-continued

```
1               5


<210> SEQ ID NO 12
<211> LENGTH: 7
<212> TYPE: PRT
<213> ORGANISM: artificial sequence
<220> FEATURE:
<223> OTHER INFORMATION: Synthetic Construct

<400> SEQUENCE: 12

Leu Ser Leu Gly Val Gly Ala
1               5


<210> SEQ ID NO 13
<211> LENGTH: 54
<212> TYPE: DNA
<213> ORGANISM: Artificial Sequence
<220> FEATURE:
<223> OTHER INFORMATION: Synthetic sequence
<220> FEATURE:
<221> NAME/KEY: CDS
<222> LOCATION: (25)..(54)

<400> SEQUENCE: 13

cttggtacct ctagagccgc cgcc atg tct aaa aaa aga gga ggg acc aga        51
                           Met Ser Lys Lys Arg Gly Gly Thr Arg
                           1               5

tcg                                                                   54
Ser
10


<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Met Ser Lys Lys Arg Gly Gly Thr Arg Ser
1               5                   10


<210> SEQ ID NO 15
<211> LENGTH: 38
<212> TYPE: DNA
<213> ORGANISM: Artificial Sequence
<220> FEATURE:
<223> OTHER INFORMATION: Synthetic sequence

<400> SEQUENCE: 15

ttttcttttg cggccgctta ggcttgcacg ctggttgc                             38


<210> SEQ ID NO 16
<211> LENGTH: 21
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(21)
<223> OTHER INFORMATION: Reverse complement of positions 18 through 38
      of SEQ ID NO: 15
<220> FEATURE:
<221> NAME/KEY: CDS
<222> LOCATION: (1)..(21)

<400> SEQUENCE: 16
```

-continued

```
gca acc agc gtg caa gcc taa                                          21
Ala Thr Ser Val Gln Ala
1               5


<210> SEQ ID NO 17
<211> LENGTH: 6
<212> TYPE: PRT
<213> ORGANISM: Artificial sequence
<220> FEATURE:
<223> OTHER INFORMATION: Synthetic Construct

<400> SEQUENCE: 17

Ala Thr Ser Val Gln Ala
1               5
```

NUCLEIC ACID *VACCINES* FOR PREVENTION OF FLAVIVIRUS INFECTION

The present application is a 35 U.S.C. § 371 national phase application from, and which claims priority to, international application PCT/US99/12298, filed Jun. 3, 1999, which claims priority to U.S. provisional patent application Ser. No. 60/087,908, filed Jun. 4, 1998, which applications are hereby incorporated herein in their entirety.

FIELD OF THE INVENTION

This invention relates to novel vaccines for *flaviviruses*. In particular, the vaccines are recombinant nucleic acids which contain genes for structural proteins of *flaviviruses*, such as *Japanese encephalitis virus* (*JEV*). These vaccines serve as a transcriptional unit for the biosynthesis of the virus protein antigens when administered in vivo.

BACKGROUND OF THE INVENTION

*Flaviviruses* are members of the genus *Flavivirus*, which is classified within the family Flaviviridae. The *flaviviruses* are largely pathogenic to humans and other mammals. *Flaviviruses* that inflict disease on humans include *yellow fever virus. JEV, dengue virus* (including the four serotypes *dengue*-1, *dengue*-2, *dengue*-3 and *dengue*-4), *tick-borne encephalitis virus, St. Louis encephalitis virus* (*SLEV*), and others Altogether there are about 70 species currently identified (Kuno et al., J. of Virol 72, 73-83 (1998))

The *flaviviruses* generally contain three structural proteins: M, the matrix or membrane protein. E, the envelope protein, and C, the capsid protein. (Monath, in "Virology" (Fields, ed.), Raven Press, New York, 1990, pp. 763-814. Heinz and Roehrig, in "Immunochemistry of Viruses II: The Basis for Serodiagnosis and Vaccines" (van Regenmortel and Neurath, eds.), Elsevier, Amsterdam, 1990, pp. 289-305). M has a molecular weight (MW) of about 7-8 kDa; and E has a MW of about 55-60 kDa. M is synthesized as a larger precursor termed prM. The additional portion of prM is processed in the host cell to form M prior to secretion of mature virions M and E are found in the membrane or envelope of the *flavivirus* particle, and so have long been considered to constitute important immunogenic components of the viruses.

The *flaviviruses* are RNA viruses whose single stranded RNA has a length, among the various species, of about 10 kb. The C protein, whose MW is 12-14 kDa, complexes with the RNA to form a nucleocapsid complex. Several nonstructural proteins are also encoded in the RNA genome; they are termed NS1, NS2A, NS2B, NS3, NS4A, NS4B and NS5. The genome is translated within the host cell as a polyprotein, then processed co- or post-translationally into the individual gene products by viral- or host-specific proteases (FIG. 1).

The nucleotide sequences of the genomes of several *flaviviruses* are known, as summarized in U.S. Pat. No. 5,494, 671. That for *JEV* is provided by Sumiyoshi et al. (Virology: 161: 497-510 (1987)) and Hashimoto et al. (Virus Genes 1, 305-317 (1988)). The nucleotide sequences of the virulent strain SA-14 of *JEV* and the attenuated strain SA-14-14-2 used as a vaccine in the People's Republic of China are compared in the work of Nitayaphan et al (Virology: 177: 541-552 (1990))

Nucleotide sequences encoding the structural proteins of other *flavivirus* species are also known. In many cases the sequences for the complete genomes have been reported. The sequences available include *dengue type* 1 *virus* (Mason et al., Virology 161:262-267 (1987)), *dengue type* 2 *virus* (Deubel et al., Virology 155:365-377 (1986), Gruenberg et al J. Gen Virol 69, 1391-1398 (1988), Hahn et al Virology 162, 167-180 (1988)), *dengue type* 3 *virus* (Osatomi et al., Virus Genes 2:99-108 (1988)), *dengue type* 4 *virus* (Mackow et al., Virology 159:217-228 (1987), Zhao et al Virology 155: 77-88 (1986)), and *yellow fever virus* (*YFV*) (Rice et al., Science 229, 726-733 (1985))

Many *flaviviruses* including *JEV* are transmitted to humans and other host animals by mosquitoes. They therefore occur over widespread areas, and their transmission is not easily interrupted or prevented. *JEV* affects adults and children, and there is a high mortality rate among infants, children, and the elderly; in areas of tropical and subtropical Asia (Tsai et al., in "Vaccines" (Plotkin, ed.) W. B. Saunders. Philadelphia, Pa. 1994, pp. 671-713). Among survivors, there are serious neurological consequences, related to the symptoms of encephalitis, that persist after infection. In more developed countries of this region such as Japan, the Republic of China, and Korea, *JEV* has been largely controlled by use of a vaccine of inactivated *JEV*. Nevertheless, it is still prevalent in other countries of the region.

Dengue virus disease is also mosquito-borne, occurring globally in regions with tropical and sub-tropical climates. Symptoms include fever, rash, severe headache and joint pain, but mortality from dengue is low. Epidemics of dengue virus are sufficiently frequent and widespread that the disease represents a major public health problem. Nevertheless, safe and effective vaccines to protect against dengue are not available, despite decades of effort. There thus is a strong need for a vaccine against dengue.

Yellow fever is prevalent in tropical regions of South America and sub-Saharan Africa, and is transmitted by mosquitoes. Infection leads to fever, chills, severe headache and other pains, anorexia, nausea and vomiting, with the emergence of jaundice. A live virus vaccine, 17D, grown in infected chicken embryos, is considered safe and effective. Nevertheless, there remains a need for a vaccine that avoids the necessity of administering live virus, with its attendant development of mild symptoms and viremia The vaccines available for use against JEV include live virus inactivated by such methods as formalin treatment as well as attenuated virus (Tsai et al.) Whole virus vaccines, although effective, do not have certain problems and/or disadvantages The viruses are cultivated in mouse brain or in cell culture using mammalian cells as the host Such culture methods are cumbersome and expensive Furthermore, there is the attendance risk of incorporating antigens from the host cells, i.e., the brain or other host, into the final vaccine product, potentially leading to unintended and undesired allergic responses in the vaccine recipients. There is also the risk of inadvertent infection among workers involved in vaccine production. Finally, there is the risk that the virus may not be fully or completely inactivated or attenuated, and thus, the vaccine may actually cause disease A recombinant *flavivirus* which is a chimera between two *flaviviruses* is disclosed in WO 93/06214 The chimera is a construct fusing non-structural proteins from one "type", or serotype, of *dengue viruses* or a *flavivirus*, with structural proteins from a different "type", or serotype, of *dengue virus* or another *flavivirus*. The second *flavivirus* may be *JEV*

Several recombinant subunit and viral vaccines have been devised in recent years. U.S. Pat. No. 4,810,492 describes the production of the E glycoprotien of *JEV* for use as the antigen in a vaccine. The corresponding DNA is cloned into an expression system in order to express the antigen protein in a suitable host cell such as *E. coli,* yeast, or a higher organism cell culture. U.S. Pat. No. 5,229,293 discloses recombinant baculovirus harboring the gene for *JEV* E protein. The virus is used to infect insect cells in culture such that the E protein is produced and recovered for use as a vaccine U.S. Pat. No. 5,021,347 discloses a recombinant vaccinia virus into whose genome the gene for *JEV* E protein has been incorporated. The live recombinant vaccinia virus is used as the vaccine to immunize against *JEV* Recombinant vaccinia and baculoviruses in which the viruses incorporate a gene for a C-terminal truncation of the E protein of *dengue type* 2, *dengue type* 4, and *JEV* are disclosed in U.S. Pat. No. 5,494, 671. U.S. Pat. No. 5,514,375 discloses various recombinant vaccinia viruses which express portions of the *JEV* open reading frame extending from prM to NS2B These pox viruses induced formation of extracellular particles that contain the processed M protein and the E protein. Two recombinants encoding these *JEV* proteins produced high titers of neutralizing and hemagglutinin-inhibiting antibodies, and protective immunity, in mice. The extent of these effects was greater after two immunization treatments than after only one. Recombinant vaccinia virus containing genes for the M and E proteins of *JEV* conferred protective immunity when administered to mice (Konishi et al., Virology 180: 401-410 (1991)). HeLa cells infected with recombinant vaccinia virus bearing genes for prM and E from JEV were shown to produce subviral particles (Konishi et al., Virology 188: 714-720 (1992)) Dmitriev et al. report immunization of mice with a recombinant vaccinia virus encoding structural and certain nonstructural proteins from *tick-borne encephalitis virus* (J Biotechnol 44:97-103 (1996)).

Recombinant virus vectors have also been prepared to serve as virus vaccines for dengue fever Zhao et al. (J. Virol 61, 4019-4022 (1987)) prepared recombinant vaccinia virus bearing structural proteins and NS1 from *dengue type* 4 and achieved expression after infecting mammalian cells with the recombinant. Similar expression was obtained using recombinant baculovirus infecting target insect cells (Zhang et al. J. Virol. 62, 3027-3031(1988)). Bray et al. (J. Virol. 63, 2853-2856 (1989)) also report a recombinant vaccinia *dengue* vaccine based on the E protein gene that confers protective immunity on mice when challenged to develop dengue encephalitis. Falgout et al. (J. Virol 63, 1852-1860 (1989)) and Falgout et al. J. Virol. 64, 4356-4363 (1990) report similar results. Zhang et al. (J. Virol 62, 3027-3031 (1988)) showed that recombinant baculovirus encoding *dengue* E and NS1 proteins likewise can protect mice against dengue encephalitis when challenged. Other combinations in which structural and nonstructural genes are incorporated into recombinant virus vaccines fail to produce significant immunity (Bray et al. J. Virol. 63, 2853-2856 (1989)) Also, monkeys failed to develop fully protective immunity to *dengue virus* challenge when immunized with recombinant baculovirus expressing the E protein (Lai et al (1990) pp 119-124 in F. Brown, R. M. Chancock, H. S. Ginsberg and R. Lerner (eds) "Vaccines 90. Modern approaches to new vaccines including prevention of AIDS", Cold Spring Harbor Laboratory, Cold Spring Harbor, N.Y.).

Immunization using recombinant DNA preparations has been reported for *St. Louis encephalitis virus* (*SLEV*) and *dengue*-2 *virus* using weanling mice as the model (Phillpotts et al., Arch Virol. 141, 743-749 (1996), Kochel et al., Vaccine 15 547-552 (1997)) Plasmid DNA encoding the prM and E genes of *SLEV* provided partial protection against *SLEV* challenge with a single or double dose of DNA immunization In these experiments control mice exhibited about 25% survival, and no protective antibody was detected in the DNA immunized mice (Phillpotts et al.). In mice that received three intradermal injections of recombinant *dengue*-2 plasmid DNA containing prM, 100% developed anti-*dengue*-2 neutralizing antibodies, and 92% of those receiving the corresponding E gene likewise developed neutralizing antibodies (Kochel et al) Challenge experiments using a two-dose schedule, however, failed to protect mice against lethal *dengue*-2 *virus* challenge.

The vaccines developed to date for immunizing against JEV have a number of disadvantages and problems attending their use. Inactivated virus vaccine is costly and inconvenient to prepare. In addition, it carries the risk of allergic reaction originating from proteins of the host used in preparing the virus. Furthermore, it presents considerable risk to the workers employed in their production. Candidate attenuated *JEV* vaccines are undergoing clinical trials but as of 1996 have not found wide acceptance outside of the People's Republic of China (Hennessy et al., Lancet 347: 1583-1586 (1996)). Recombinant vaccines based on the biosynthetic expression of only certain of the proteins of the *JEV* genome appear not to induce high antibody titers, and, as with the whole virus preparations, carry the risk of adverse allergic reaction to antigens from the host organism, or to the vaccinia virus vector, as the case may be. Similar problems attend the preparation of vaccines against *YFV* Vaccine development against *dengue* is less advanced, and such virus-based or recombinant protein-based vaccines face similar problems as those just alluded to There is therefore a need for vaccines directed against *flaviviruses* such as *yellow fever, dengue, JEV*, and *SLEV* which are inexpensive to prepare, present little risk to workers involved in their manufacture, carry minimal risk of adverse immunological reactions due to impurities or adventitious immunogenic components, and are highly effective in eliciting neutralizing antibodies and protective immunity There is furthermore a need for a vaccine against *JEV* and related *flaviviruses* that minimizes the number of immunizing doses required.

SUMMARY OF THE INVENTION

The present invention provides a nucleic acid molecule which contains a transcriptional unit (TU) for an immunogenic *flavivirus* antigen. The TU directs a host cell, after being incorporated within the cell, to synthesize the antigen. In an important aspect of the invention, the *flavivirus* is either *yellow fever virus* (*YFV*), *dengue type* 1 *virus, dengue type* 2 *virus, dengue type* 3 *virus, dengue type* 4 *virus, St. Lous encephalitis virus* (*SLEV*), or *Japanese encephalitis virus* (*JEV*) In important embodiments of the present invention, the antigen may be the *flavivirus* M protein, the E protein, or both In particular, when the TU is for both the M and E proteins, the host cell secretes subviral particles containing the M and E antigens In a further important aspect of the invention, the nucleic acid is a DNA molecule. In additional significant embodiments, the nucleic acid TU includes a control sequence disposed appropriately such that it operably controls the expression of the M and E antigens; this control sequence may advantageously be the cytomegalovirus immediate early promoter. In an additional embodiment the transcriptional unit also includes a poly-A terminator.

The present invention further provides a host cell harboring a nucleic acid molecule which includes a transcriptional unit for an immunogenic *flavivirus* antigen that directs the host cell to synthesize the immunogenic antigen. The *flavivirus* may be *YFV, dengue type* 1 *virus, dengue type* 2 *virus, dengue type* 3 *virus, dengue type* 4 *virus, SLEV*, or *JEV*. In important embodiments, the antigen may be the M protein, the E protein, or both the M and the E proteins; in the latter case, the cell secretes subviral particles containing the M and E antigens Additionally the invention provides a composition for vaccinating a subject against a *flavivirus* containing a nucleic acid molecule that includes a transcriptional unit for an immunogenic flaviviral antigen. The transcriptional unit directs a cell within the body of the subject, after being incorporated therein, to synthesize the immunogenic antigen. The composition further includes a pharmaceutically acceptable carrier In significant embodiments, the *flavivirus* may be *yellow fever virus, dengue type* 1 *virus, dengue type* 2 *virus, dengue type* 3 *virus, dengue type* 4 *virus, SLEV,* or *JEV* Furthermore, the antigen may be the M protein, the E protein, or both the M and the E proteins, in the latter instance the cell secretes subviral particles comprising the *flavivirus* M and E antigens. In important embodiments, the nucleic acid molecule is a DNA molecule. In further significant embodiments, the transcriptional unit additionally contains a control sequence disposed appropriately such that it operably controls the expression of the M and E antigens when the nucleic acid is introduced into the cell of the subject; advantageously the control sequence is the cytomegalovirus immediate early promoter. In a still further embodiment, the transcriptional unit also includes a poly-A terminator The invention provides still further a method of immunizing a subject against infection by a *flavivirus*. The method involves administering to the subject an effective amount of a vaccinating composition that contains a nucleic acid molecule which includes a transcriptional unit for an immunogenic *flavivirus* antigen. The transcriptional unit directs a cell within the body of the subject, after being taken up by the cell, to synthesize the immunogenic antigen. The composition additionally includes a pharmaceutically acceptable carrier. In significant embodiments of the method, the *flavivirus* may be *yellow fever virus, dengue type* 1 *virus, dengue type* 2 *virus, dengue type* 3 *virus, dengue type* 4 *virus, SLEV,* or *JEV*. In yet other important aspects of the method, the antigen may be the M protein, the E protein, or both the M and the E proteins. When the antigen is both the M and the E protein, the cell within the body of the subject, after incorporating the nucleic acid within it, secretes subviral particles comprising the flaviviral M and E antigens. Additionally, in significant embodiments of the method, the vaccinating composition is administered to the subject in a single dose, and is administered via a parenteral route. In yet a further aspect of the method, the nucleic acid is a DNA molecule. In yet additional embodiments of the method, the transcriptional unit further includes a control sequence disposed appropriately such that it operably controls the expression of the M and E antigen, in a significant aspect of this embodiment, the control sequence is the cytomegalovirus immediate early promoter Furthermore, the transcriptional unit may further include a poly-A terminator.

These aspects and embodiments of the invention are the basis for its distinct attributes and advantages. Being a nucleic acid construct involving only portions of the *flavivirus* genome rather than the sequence encompassing the complete genome, the nucleic acid TU-containing vaccine is completely nonviable. It therefore poses no danger of infection by the *flavivirus* to those involved in its manufacture, and none to subjects receiving the vaccine The nucleic acid vaccine is easy to prepare and to administer, and is stable to storage prior to use. Unexpectedly it has been found that the nucleic acid vaccine of the invention is essentially 100% successful in conferring protecting immunity in mammals after administering only a single dose. A further unexpected result is that the nucleic acid TU is able to engender immunity to a *flavivirus* in a female mammal which can be transmitted to its progeny through the milk. Without wishing to be limited by theory, the inventory believes that a possible mechanism for the success of the nucleic acid is conferring protective immunity is that a host cell harboring the nucleic acid, such as the cell of a subject to whom the vaccine is administered, produces subviral particles containing the flaviviral M and E antigens. These particles may closely mimic the immunogenic attributes of virulent *flaviviruses* themselves.

DETAILED DESCRIPTION OF THE INVENTION

Figure 1:
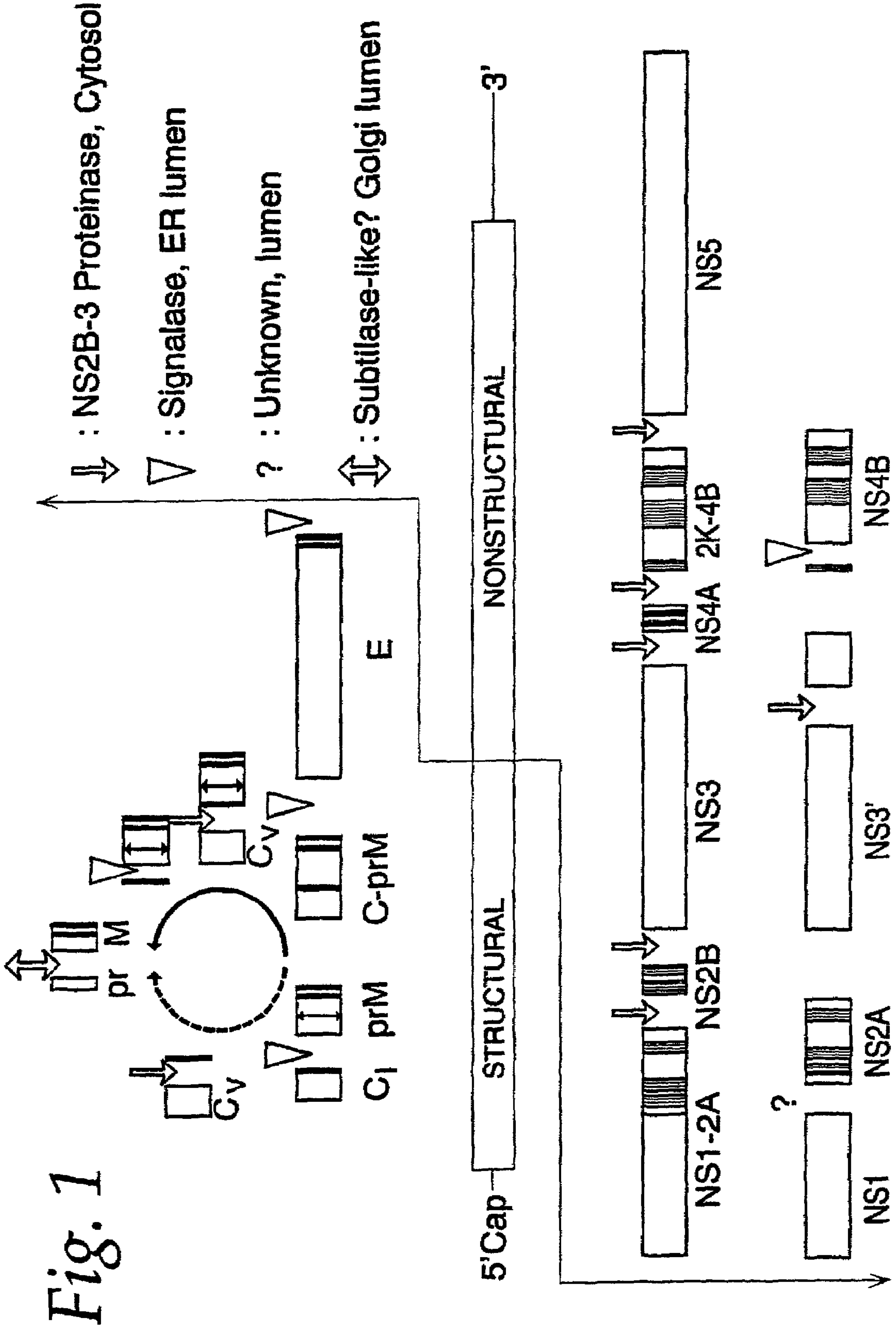
FIG. 1 is a schematic representation of flaviviral polyprotein processing. The central horizontal region provides a schematic representation of the viral genome. The lines denote the 5' and 3' non-translated regions and the boxed regions represent the open reading frame for structural (left and top) and non-structural (right and bottom) proteins. Cleavage by host cell signalase occurs simultaneously with translation at the E protein C-terminus separating structural and non-structural regions. A subtilase-like cellular enzyme, furin, may be responsible for prM cleavage. Potential transmembrane domains of viral polyprotein are indicated by shaded areas.

The invention encompasses nucleic acid transcriptional units which encode flaviviral antigenic proteins, such as the M and E protein antigens. The nucleic acids function to express the M and E protein antigens when the nucleic acid is taken up by an appropriate host cell, especially when the host cell is the cell of a subject. The invention also encompasses a vaccine whose active agent is the nucleic acid transcriptional unit (TU). The invention further encompasses the cultured host cells when they contain within them a nucleic acid TU. The invention in addition encompasses a method of immunizing a subject against flaviviral infection by administering to the subject an effective amount of a vaccine containing the nucleic acid TU molecules As used herein, "nucleic acid transcriptional unit" or "nucleic acid transcriptional unit molecule" relates to a nucleic acid encoding one or more specified genes. The TU has the biological activity that, after having been introduced into a suitable host cell, the nucleic acid induces the biosynthesis of one or more specified gene products encoded by the specified gene or genes. The gene product(s) is (are) other biological macromolecules, such as proteins, not chemically related to the TU. The nucleic acid TU induces the cell to employ its cellular components to produce the specific gene product or products whose gene or genes are contained in the TU Although any nucleic acid may serve as a TU, in a preferred embodiment, the TU is the DNA of a plasmid or similar vector, wherein the plasmid or vector encompasses in addition coding sequences for marker genes or other sequence constructions that facilitate experimentation and biosynthesis of the TU.

As used herein, a "control sequence" is a regulatory nucleotide sequence incorporated within a nucleic acid TU which interacts with appropriate cellular components of the host cell and leads to enhanced or activated biosynthesis of the gene products encoded by the TU. Thus a suitable control sequence is one with which the components of the host cell have the capability to interact, resulting in stimulated synthesis of the gene product. When operably disposed in a nucleic acid with respect to a specified gene, a control sequence effectively controls expression of the specified gene.

As used herein, a "promoter" is a nucleotide sequence in a nucleic acid TU which serves as a control sequence.

As used herein, a "terminator" is an extended nucleotide sequence which acts to induce polyadenylation at the 3' end of a mature mRNA. A terminator sequence is found after, or downstream from, a particular coding sequence.

As used herein, a "host cell" is a prokaryotic or eukaryotic cell harboring a nucleic acid TU coding for one or more gene products, or into which such a TU has been introduced. Thus a host cell harbors a foreign or heterologous substance, the TU, which is not naturally or indigenously found in it as a component. A suitable host cell is one which has the capability for the biosynthesis of the gene products as a consequence of the introduction of the TU In particular, a suitable host cell is one which responds to a control sequence and to a terminator sequence, if any, that may be included within the TU In important embodiments of the present invention, the host cell is a mammalian cell In particularly important embodiments of this invention, the host cell is a naturally occurring cell in the body of a human or nonhuman subject to whom (which) the TU has been administered as a component of a vaccine Alternatively, in analytical, or diagnostic applications, or for demonstrative purposes, the mammalian cell may be a human or nonhuman cell cultured in vitro.

As used herein, a "vaccine" or a "composition for vaccinating a subject" specific for a particular pathogen relates to a preparation, which, when administered to a subject, leads to an immunogenic response in a subject. As used herein, an "immunogenic" response is one that confers upon the subject protective immunity against the pathogen. Without wishing to be bound by theory, it is believed that an immunogenic response may arise from the generation of neutralizing antibodies, or from cytotoxic cells of the immune system, or both. As used herein, an "immunogenic antigen" is an antigen which leads to an immunogenic response when it is introduced into a subject, or, as in the case of the present invention, when it is synthesized within the cells of a host or a subject As used herein, an "effective amount" of a vaccine or vaccinating composition is an amount which, when administered to a subject, is sufficient to confer protective immunity upon the subject. Historically, a vaccine has been understood to contain as an active principle one or more specific molecular components or structures which comprise the pathogen, especially its surface. Such structures may include surface components such as proteins, complex carbohydrates, and/or complex lipids which commonly are found in pathogenic organisms As used herein, however, it is to be stressed that the terms "vaccine" or "composition for vaccinating a subject" extend the conventional meaning summarized in the preceding paragraph As used herein, these terms also relate to the nucleic acid TU molecule of the instant invention or to compositions containing the TU The TU induces the biosynthesis of one or more specified gene products encoded by the TU within the cells of the subject, wherein the gene products are specified antigenic proteins of the pathogen. The biosynthetic antigens then serve as the immunogen. As already noted, the TU, and hence the vaccine, may be any nucleic acid that bears specified genes for the specified immunogenic antigens. In a preferred embodiment of this invention, the TU of the vaccine is a DNA. The TU may be a plasmid or vector incorporating additional genes or particular sequences for the convenience of the skilled worker in the fields of molecular biology, cell biology, and viral immunology (See "Molecular Cloning A Laboratory Manual", 2nd Ed., Sambrook, Fritsch and Maniatis. Cold Spring Harbor Laboratory, Cold Spring Harbor, N.Y. 1989, and "Current Protocols in Molecular Biology", Ausubel et al., John Wiley and Sons, New York 1987 (updated quarterly), which are incorporated herein by reference)

The nucleic acid TU molecules of the instant invention designate nucleic acids, or derivatives of nucleic acids, whose nucleotide sequences encode specific gene products related to antigenic proteins of *flaviviruses* such as *JEV, dengue, yellow*

*fever virus* and *St. Lous encephalitis virus*. Although any nucleic acid may serve as a TU, in an important embodiment, the TU is a DNA. Alternatively, the nucleic acids may be RNA molecules They may also be any one of several derivatives of DNA or RNA whose backbone phosphodiester bonds have been chemically modified to increase the stability of the TU as a pharmaceutical agent Modifications so envisioned include, but are not limited to, phosphorothioate derivatives or phosphonate derivatives; these and other examples of derivatives are well known to persons skilled in the field of nucleic acid chemistry

Figure 2:
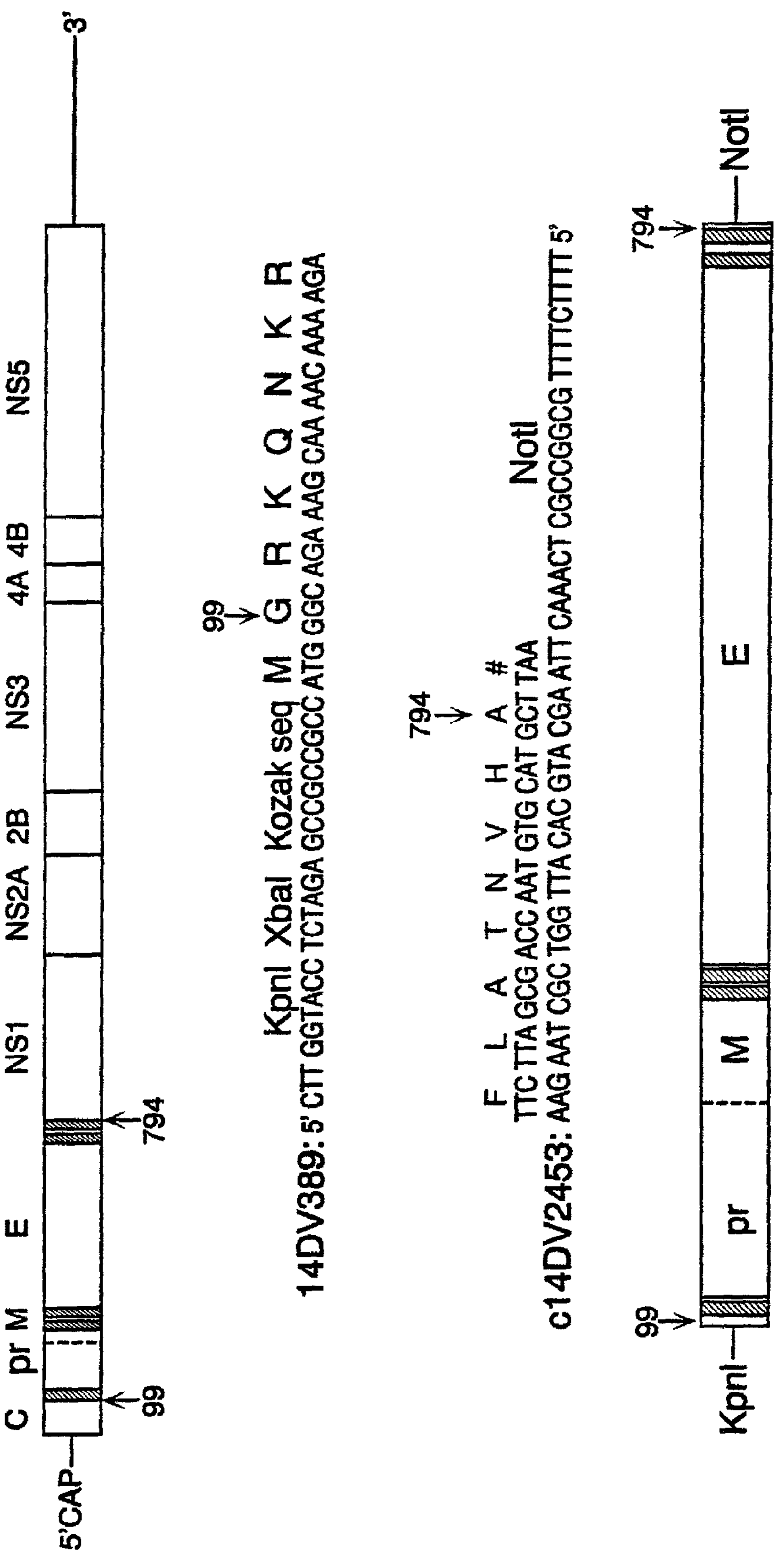
FIG. 2 presents a map of the *JEV* genome (top), the DNA sequence of oligonucleotides (SEQ ID NOs: 1, 3, 4) used in a reverse transcriptase-polymerase chain reaction (PCR) (center) to construct the transcription unit for the expression of prM-E protein coding regions (bottom). Potential transmembrane domains of viral polyprotein are indicated by shaded areas. The amino acid sequences (SEQ ID NOs: 2 and 5) encoded by the oligonucleotides are also shown.

*JEV* is an RNA virus whose genome has been characterized and sequenced (see FIGS. 1 and 2). The gene for the M structural gene includes a pre-M sequence (prM) which is translated intracellularly. This sequence allows assembly of *JEV* particles intracellularly. The pre-M sequence is then cleaved from the gene product to yield virus particles containing mature M proteins prior to secretion. Related *flaviviruses*, such as *YFV, dengue*, and *SLEV*, have similar genomic structures and functions (see, for example, FIGS. 6 and 7).

An important TU for flaviviral M and E proteins in the instant invention is a DNA In accord with the discussion in the preceding paragraph, this DNA encodes the gene for M comprising the pre-M sequence as well, it also encodes the gene for the E protein. In this way the intended gene products are enabled to form subviral particles within the host cell The host cell then may cleave the pre-M sequence in a fashion analogous to that which occurs with respect to replete virions In order to function effectively in vivo or a vaccine, it is advantageous to include within the nucleic acid TU a control sequence that has the effect of enhancing or promoting the translation of the sequences encoding the antigens. Use of such promoters is well known to those of skill in the fields of molecular biology, cell biology, and viral immunology (See "Molecular Cloning A Laboratory Manual", 2nd Ed. Sambrook, Fritsch and Maniatis, Cold Spring Harbor Laboratory, Cold Spring Harbor, N.Y., 1989, and "Current Protocols in Molecular Biology", Ausubel et al., John Wiley and Sons, New York 1987 (updated quarterly)) Since the nucleic acid TU is intended for use as a vaccine in a mammalian host, the promoter to be employed is preferably one which operates effectively is mammalian cells Such a promoter is disposed with respect to the genes whose translation is to be promoted, at a position at which it may operable promote such translation In a significant embodiment of the instant invention, this promoter is the cytomegalovirus early promoter In addition, in a further preferred embodiment of the invention, the genes are followed, in the TU nucleic acid, by a terminator sequence (Sambrook et al.). Particular embodiments of the invention relate to both prokaryotic and eukaryotic host cells. Many promoter sequences are known that are useful in either prokaryotic or eukaryotic host cells. (See Sambrook et al.)

Preparation of the nucleic acid TU of the invention is readily accomplished by methods well known to workers of skill in the field of molecular biology. Procedures involved are set forth, for example, in Sambrook, Fritsch and Maniatis, Cold Spring Harbor Laboratory, Cold Spring Harbor, N.Y., 1989, and "Current Protocols in Molecular Biology", Ausubel et al., John Wiley and Sons, New York 1987 (updated quarterly) The flaviviral RNA molecule may be isolated from a sample of live virus by methods widely known among virologists familiar with flavirridae, for example, and with other groups of viruses as well. Methods used with *JEV* are summarized in Kuno et al (1990) The RNA is used as a template for the synthesis of cDNA using reverse transcriptase From the cDNA, a fragment containing the pre-M through E gene (see FIG. 2) may be obtained by digestion with restriction nucleases known to cleave the cDNA appropriately to provide such fragments Examples of restriction digestion of *JEV*, for example, are provided in Nitayaphan et al (1990) and Konishi et al (1991) Incorporation of promoters, such as the cytomegalovirus promoter, and of the polyadenylation signal, is likewise well known to skilled practitioners in molecular biology and recombinant DNA engineering When a nucleic acid harboring a TU containing the desired genes and control sequences is prepared, it may be obtained in larger quantities by methods that amplify a nucleic acid fragment Such methods are widely known to workers skilled in molecular biology and recombinant DNA engineering Examples of these methods include incorporation of the nucleic acid fragment into a plasmid for replication by culturing in a cell such as a prokaryotic cell and harvesting the plasmid after completing the culture, as well as amplification of the nucleic acid fragment by methods using the polymerase chain reaction. These examples are not intended to limit the ways in which the nucleic acid containing the TU may be obtained The TU-containing nucleic acid molecules of the instant invention may be introduced into appropriate host cells in many ways well known to skilled workers in the fields of molecular biology and viral immunology. By way of example, these include, but are not limited to , incorporation into a plasmid or similar nucleic acid vector which is taken up by the host cells, or encapsulation within vesicular lipid structures such as liposomes, especially liposomes comprising cationic lipids, or adsorption to particles that are incorporated into the host cell by endocytosis.

In general a host cell is a prokaryotic or eukaryotic cell harboring a nucleic acid TU, or into which such a TU molecule has been introduced. The TU of the present invention induces the intracellular biosynthesis of the encoded E and M antigens A suitable host cell is one which has the capability for the biosynthesis of the gene products as a consequence of the introduction of the nucleic acid In particular embodiments of the invention, a suitable host cell is one which responds to a control sequence and to a terminator sequence, if any, which may be included within the TU In order to respond to this fashion, such as host cell contains within it components which interact with a control sequence and with a terminator and act to carry out the respective promoting and terminating functions When the host cell is cultured in vitro, it may be a prokaryote, a single-celled eukaryote or a mammalian cell. In particular embodiments of the present invention, the host cell is a mammalian cell. In these cases, the synthesized E and M protein gene products are available for use in analytical, or diagnostic applications, or for demonstrative purposes In favorable circumstances, such as when the host cell is a cultured mammalian cell, the E and M antigens are secreted in the form of subviral particles These are aggregates of E and M proteins resembling live virus in surface ultrastructural morphology and immunogenic properties. Since the nucleic acid TU of the invention does not include the remainder of the flaviviral genone, however, there is no capsid incorporated, and most importantly, no infectious viral RNA.

In another important embodiment of this invention, the host cell is a natural cellular component of the subject to whom the TU has been administered as a vaccine The nucleic acid TU, when so administered, is understood to be taken up by the cells of the subject, whereby those cells become host cells as used herein. The subject's cells have the capability of responding to any promoter sequences, and terminator, if present. In any case, the TU nucleic acid induces the subject's cells to synthesize flaviviral E and M gene products. Without wishing to be constrained by theoretical considerations, it is believed that the subject's host cells produce subviral particles in vivo consisting of the M and E antigens, just as has been found to occur with cultured mammalian host cells in vitro. Such subviral particles, it is believed, then serve as the in vivo immunogen, stimulating the immune system of the subject to generate immunological responses which confer protective immunity on the subject. Again without wishing to be limited b theory, the resulting protective immunity may arise via either humoral or cellular immunity, i.e., via either an MHC class II- or class I-restricted mechanisms, respectively, or by both mechanisms According to the invention, subjects may be immunized against infection by *flaviviruses*, such as *JEV, YFV, dengue*, and *SLEV*, by administering to them an effective amount of a nucleic acid TU encoding genes for the M and E antigens The nucleic acid, after being incorporated into the cells of the subject, leads to the synthesis of the flaviviral M and E antigens In order to administer the nucleic acid TU to the subject, it is incorporated into a composition which comprises as well a pharmaceutically acceptable carrier. Such carriers are well known to those of skill in pharmaceutical science They include water for injection, and common physiological buffers (Remington, Pharmaceutical Sciences) They may also include vesicle or liposome structures, especially those containing cationic lipids, as is known to skilled workers in the fields of pharmaceutical science and immunology.

An effective amount of a vaccinating composition is readily determined by those of skill in the field of viral immunology to be an amount which, when administered to a subject, confers protective immunity upon the subject. In order to undertake such a determination, the skilled artisan may assess the ability to induce flaviviral M- and E-specific antibodies and/or flaviviral M- and E-specific cytotoxic T lymphocytes present in the blood of a subject to whom the vaccine has been administered One may in addition determine the level of protective immunity conferred upon an experimental animal by challenge with live *JEV*. Such challenge experiments are well known to workers of skill in viral immunology. In general, in order to immunize a subject against infection by *JEV, YFV, degue*, or *SLEV*, according to the present invention, and recognizing that the nucleic acid TU molecules employed in such methods may have differing overall sizes, doses ranging from about 0.1 μg/kg body weight to about 50 μg/kg body weight may be used.

It has unexpectedly been found that a TU of the present invention which is a DNA confers protective immunity at a level of effectiveness approximating 100% after administration of only a single effective dose of the TU. This is in contrast to many immunization methods carried out using conventional vaccines (as described above), which frequently require one or more booster vaccinations and which may not confer protective immunity to an effectiveness near 100%

It has further been found unexpectedly that protective immunity may be transmitted from a vaccinated female subject to the offspring of the subject A significant proportion of neonatal mice was shown to be protected against viral challenge after their mothers were vaccinated using the TU DNA of the invention Without wishing to be limited by theory, it is known that passive immunity may be conferred on neonatal mammals due to the presence in material milk of neutralizing antibodies specific for various pathogens. It is possible that the protective immunity against *JEV* found with the neonates was transmitted to them in this way Particular embodiments of the present invention are set forth in the examples which follow. These examples are not intended to limit the scope of the invention as disclosed in this specification.

EXAMPLES

General methods utilizing molecular biology and recombinant DNA techniques related to preparing and expressing the nucleic acid TU molecules of the invention are set forth in, for example, "Current Protocols in Molecular Biology", Ausubel et al., John Wiley and Sons, New York 1987 (updated quarterly), and Molecular Cloning A Laboratory Manual 2nd Ed., Sambrook, Fritsch and Maniatis, Cold Spring Harbor Laboratory, Cold Spring Harbor, N.Y., 1989.

Example 1

Preparation of Recombinant Plasmids Containing the Transcriptional Unit Encoding *JEV* prM and E Antigens Genomic RNA was extracted from 150 μL of *JEV* strain SA 14 virus seed grown from mouse brain using a QIAAMP™ Viral RNA Kit (Qiagen, Santa Clarita, Calif.). RNA, adsorbed on a silica membrane, was eluted in 80 μL of nuclease-free water, and used as a template for the amplification of *JEV* prM and E gene coding sequences. Primer sequences were obtained from the work of Nitayaphan et al. (1990). A single cDNA fragment containing the genomic nucleotide region 389-2478 was amplified by the reverse transcriptase-polymerase chain reaction (RT-PCR). Restriction sites Kpnl and XbaI, the consensus Kozak ribosomal binding sequence, and the translation initiation site were engineered at the 5' terminus of the cDNA by amplimer 14DV389 (SEQ ID NO:1). An in-frame translation termination codone, followed by a NotI restriction site, was introduced at the 3' terminus of the cDNA by amplimer c14DV2453 (SEQ ID NO: 3) (see FIG. 2). One-tube RT-PCR was performed using a Titan RT-PCR Kit (Boehringer Manheim, Indianapolis, Ind.). 10 μL of viral RNA was mixed with 1 μL each of 14DV389 (50 μM) and c14DV2453 (50 μM) and 18 μL of nuclease-free water and the mixture was heater at 85° C. for 5 min and then cooled to 4° C. 75 μL of reaction mix [20 μL 5x buffer, 2 μL of dNTP mixture (10 mM each), 5 μL of dithiothreitol (0.1 mM), 0.5 μL of RNASIN™ RNAse inhibitor (40 U/μL, Boehringer Mannheim), 2 μL of polymerase mixture, and 45.5 μL of nuclease-free water] was added and RT-PCR performed as follows: 1 cycle (50° C. for 30 min, 94° C. for 3 min, 50° C. for 30 s, 68° C. for 2.5 min), 9 cycles (94° C. for 30 s, 50° C. for 30 s, 68° C. for 2.5 min), 20 cycles (94° C. for 30 s, 50° C. for 30 s, 68° C. for 2.5 min in the first cycle, with an increment of 5 s per cycle thereafter), and a final extension at 68° C. for 15 min. The RT-PCR product was purified by a QIAQUICK™ PCR Purification Kit (Qiagen) and eluted with 50 μL of 1 mM Tris-HCl, pH 7.5.

All vector constructions and analyses were carried out by using standard techniques (Sambrook et al., 1989) RT-PCR amplified cDNA, digested with Kpnl and NotI nucleases, was inserted into the KpnI-NotI site of eukaryotic expression plasmid vector (pCDNA2, Invitrogen, Carlsbad, Calif.). Electroporation-competent *Escherichia coli* XL1-Blue Cells (Stratagene, La Jola, Calif.) were transformed by electroporation (Gene Pulser™, Bio-Rad, Hercules, Calif.) and plated onto LB agar plates containing 100 μg/mL carbenicillin (Sigma Chemical Co., St. Louis, Mo.). Clones were picked and inoculated into 3 mL LB broth containing 100 μg/mL carbenicillin. Plasmid DNA was extracted from a 14 h culture using a QIAprep™ Spin Miniprep Kit (Qiagen). Automated DNA sequencing was performed as recommended (Applied Biosystems/Perkin Elmer, Foster City, Calif.). Both strands of the cDNA were sequenced and shown to be identical to the sequence for the original SA14 strain (Nitayaphan et al., 1990)

Figure 3:
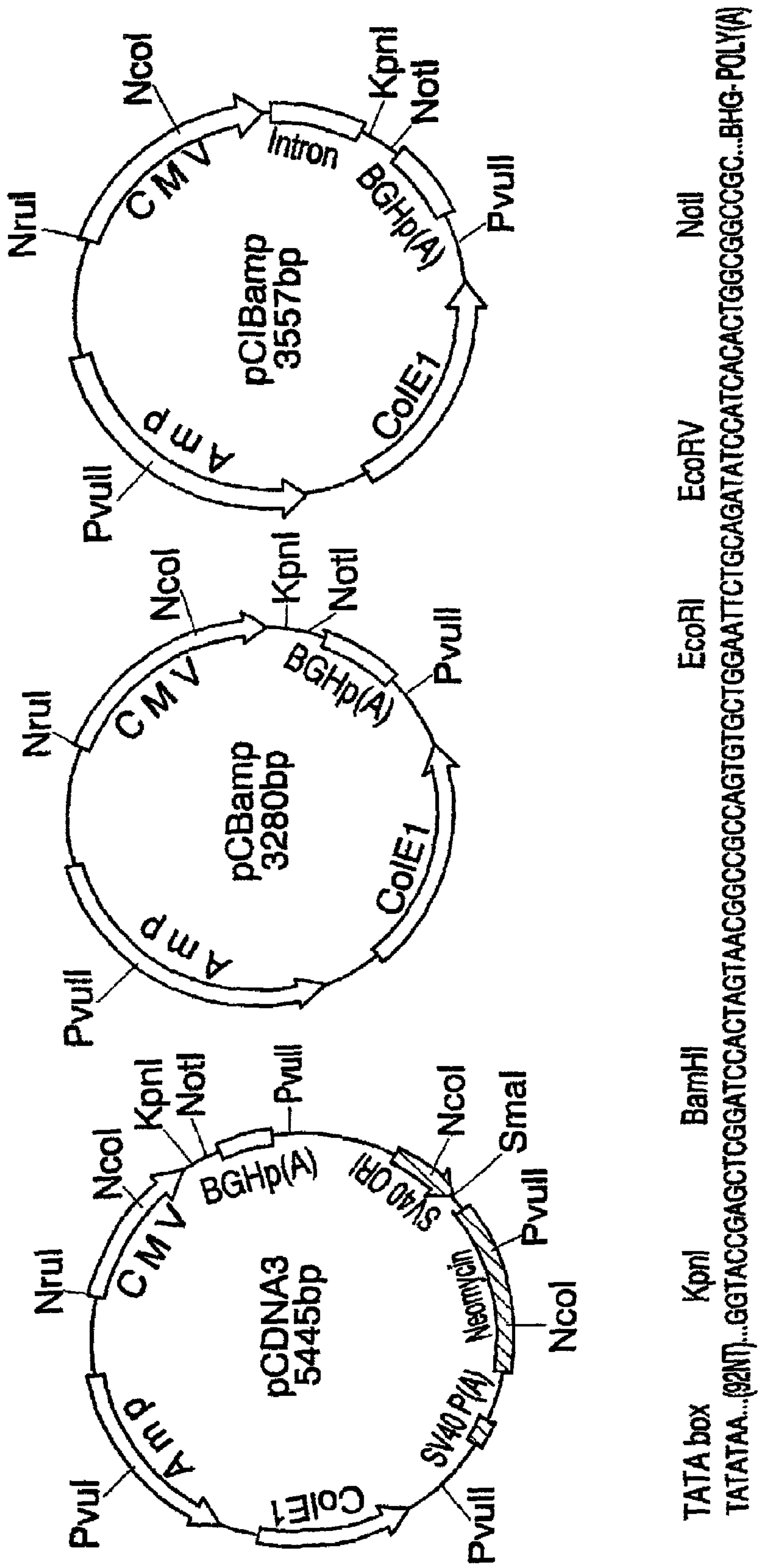
FIG. 3 shows a schematic representation of the plasmid vectors, pCDNA3, pCBamp, and PCIBamp, and the relationship between them. These plasmids include the CMV (cytomegalovirus) promoter/enhancer element, BGHp(A) (bovine growth hormone polyadenylation signal and transcription termination sequence), ampicillin resistance gene and ColE1 origin of replication for selection and maintenance of *E. coli*. The f1 origin of replication for single-stranded rescue in *E. coli* cells, SV40 origin replication (SV40 ORI), neomycin resistance coding region, and SV40p (A) sequences were deleted from pCDNA3 to generate pCBamp. An intron sequence was inserted in the NcoI-KpnI site of pCBamp to generate plasmid pCIBamp. The multiple cloning site (SEQ ID NO: 7) for the insertion of genes for flaviviral structural proteins, located between the TATA box (SEQ ID NO:6) of the CMV promoter/enhancer and BGHp (A), is shown.

The fragment of plasmid pCDNA3 (Invitrogen, Carlsbad, Calif.) from nucleotide (nt) 1289 to nt 3455, containing f1 ori, SV40 ori, the neomycin resistance gene, and SV40 poly(A) elements was deleted by PvuII digestion and then ligated to generate the pCBamp plasmid. The vector pCIBamp, containing a chimeric intron insertion at the NcoI/KpnI site of the pCBamp was constructed by excising the intron sequence from pC1 (Promega, Madison, Wis.) by digestion with NcoI and KpnI The resulting 566-bp fragment was cloned into pCBamp by digesting with NcoI-KpnI to replace its 289-bp fragment FIG. 3 presents the relationships between the plasmids pCDA3, pCBamp, and PCIBamp Plasmids containing the transcriptional unit encoding *JEV* prM and E proteins were prepared from these plasmids. The cDNA fragment containing the *JEV* prM and E coding regions in the recombinant plasmid pCDJE2-7, derived from the pCDNA3 vector, was excised by digestion with NotI and KpnI or XbaI and cloned into the KpnI-NotI site of pCBamp, pCIBamp, pCEP4 (Invitrogen, Carlsbad, Calif.), or pREP4 (Invitrogen, Carlsbad, Calif.), or into the SpeI-NotI site of pRc/RSV (Invitrogen, Carlsbad, Calif.) expression vector to create pCBJE1-14, pCIBJES14, pCEJE, pREFE, and pRCJE, respectively. Both strands of the cDNA from clones of each plasmid were sequenced and recombinant clones with the correct nucleotide sequence were identified. Plasmid DNA for use in the in vitro transformation of mammalian cells or mouse immunization experiments was purified by anion exchange chromatography using an EndoFree™ Plasmid Maxi Kit (Qiagen).

Example 2

Evaluation of *JEV* prM and E Proteins Expressed By Various Recombinant Plasmids Using an Indirect Immunofluorescent Antibody Assay The expression of *JEV* specific gene products by the various recombinant expression plasmids was evaluated in transiently transfected cell lines of COS-1, COS-7 and SV-T2 (ATCC, Rockville, Md., 1650-CRL, 1651-CRL, and 163.1-CCL, respectively) by indirect immunofluorescent antibody assay (IFA) The SV-T2 cell line was excluded from further testing since a preliminary result showed only 1-2% of transformed SV-T2 cells were *JEV* antigen positive For transformation, cells were grown to 75% confluence in 150 $cm^2$ culture flasks, trypsinized, and resuspended at 4° C. in phosphate buffered saline (PBS) to a final cell count $5\times10^6$ per mL 10 μg of plasmid DNA was electroporated into 300 μL of cell suspension using a BioRad Gene Pulse™ (Bio-Rad) set at 150 V, 960 μF and 100 Ω resistance. Five minutes after electroporation, cells were diluted with 25 mL fresh medium and seeded into a 75 $cm^2$ flask 48 h after transformation the medium was removed from the cells, and the cells were trypsinized and resuspended in 5 mL PBS with 3% normal goat serum 10 μL aliquots were spotted on slides, air dried and fixed with acetone at −20° C. for 20 min IFA was performed with acetone-fixed plasmid-transformed cells using fluorescein isothiocyanate-conjugated goat anti-mouse immunoglobulin G (Sigma Chemical Co) and *JEV* H1AF To determine the influence of various promoter and poly (A) elements on the *JEV* prM and E protein expression, COS-1 and COS-7 cell lines were transiently transformed by an equal amount of pCDEJE2-7, pCEJE, or pRCJE plasmid DNA. *JEV* antigens were expressed in both cell lines transformed by all four recombinant plasmids, thus confirming that the CMV or RSV (rous sarcoma virus) promoter and BGH or SV40 poly(A) elements were functionally active. However, the percentage of transformed cells and the level of *JEV* antigens expressed, as determined by the number of IFA positive cells and IFA intensity, respectively, differed greatly among the various plasmids (see Table 1). A significantly high percentage of COS-1 cells transformed by pCDJE2-7, pCBJE1-14 and pCIBJES14 expressed the *JEV* antigens, and the level of the expressed proteins was compatible with *JEV*-infected cells. Cells transfected with pCEJE, pREJE or pRCJE vectors, on the other hand, had a low percentage of antigen-expressing cells, as well as a low intensity fluorescence, indicating weak expression of the antigens.

In order to ascertain whether the enhanced expression of *JEV* proteins by pCDJE2-7 was influenced by the SV40-encoded eukaryotic origin of replication, the plasmid pCBJE 1-14 was constructed so that a 2166-bp fragment, containing f1 ori, SV40 ori, the neomycin resistance gene and SV40 poly(a) elements from pCDJE2-7, was deleted. A chimeric intron was then inserted into pCBJE1-14 to generate pCIBJES14. The pCIBJES14 plasmid was used to determine if the expression of *JEV* proteins could be enhanced by the intron sequence Following transformation, cells harboring both pCBJE1-14 and pCIBJES14 vectors expressed a level of *JEV* antigens similar to that observed with pCDJE2-7 (see Table 1) This result indicates that expression of *JEV* prM and E antigens by recombinant vectors is influenced only by the transcriptional regulatory elements. Neither the eukaryotic origin of replication nor the intron sequence enhanced *JEV* antigen expression in the cells used Vectors containing the CMV promoter and BGH poly(A) (see FIG. 3) were selected for further analysis

TABLE 1

Transient expression of JE prM and E proteins by various recombinant plasmids in two transferred cell lines.

| | Vector | | | | | IF A intensity/percentage of anitgen-positive cells* | |
|---|---|---|---|---|---|---|---|
| | Promotor | Intron | Poly (A) | ORI | Recombinant Plasmid | COS-1 | COS-7 |
| pCDNA3 | CMV | No | BGH | SV40 | pCDJE2-7 | 3+/40 | 3+/35 |
| pCBamp | CMV | No | BGH | No | pCBJE1-14 | 3+/45 | nd |
| pC1Bamp | CMV | Yes | BGH | No | pC1BJES14 | 3+/39 | nd |
| pCEP4 | CMV | No | SV40 | OriP | pCEJE | 2+/4 | 2+/3 |

TABLE 1-continued

Transient expression of JE prM and E proteins by various recombinant plasmids in two transferred cell lines.

| | Vector | | | | | IF A intensity/percentage of anitgen-positive cells* | |
|---|---|---|---|---|---|---|---|
| | Promotor | Intron | Poly (A) | ORI | Recombinant Plasmid | COS-1 | COS-7 |
| pREP4 | RSV | No | SV40 | OriP | pREJE | 1+/3 | 1+/2 |
| pRe/RSV | RSV | No | BGH | SV40 | pRCJE | 1+/3 | 1+/3 |
| pCDNA3 | CMV | No | BGH | SV40 | pCDNA3/CAT | — | — |

*Various cell lines were transformed with pCDNA3/CAT (negative control). pCDJE2-7. pCBJE1-14, pC1BJES14, pCEJEm pREJE, or pRCJE, Cells were trypsinized 48 hours later and tested by an indirect immunofluorescent antibody assay (IFA) with JE virus-specific HIAF. Data are presented as the intensity (scale of 1+ to 4+) and the percentage of IFA positive cells The pCDNA3/CAT transformed cells were used as the negative control.

Example 3

Selection of an in vitro Transformed, Stable Cell Line Constitutively Expressing *JEV* Specific Gene Products COS-1 cells were transformed with 10 μg of pCDJE2-7 DNA by electroporation as described in the previous example. After a 24 hr incubation in non-selective culture medium, cells were treated with neomycin (0.5 mg.mL, Sigma Chemical Co.). Neomycin-resistance colonies, which became visible after 2-3 weeks, were cloned by limited dilution in neomycin-containing medium Expression of vector-encoded *JEV* gene products was initially screened by IFA using *JEV* HIAF. One *JEV*-IFA positive clone (JE-4B) and one negative clone (JE-5A) were selected for further analysis and maintained in medium containing 200 μg/mL neomycin Authenticity of the *JEV* E protein expressed by the JE-4B clone was demonstrated by epitope mapping by IFA using a panel of *JEV* E-specific murine monoclonal antibodies (Mab) (Kimura-Kuroda et al., J Virol (45, 124-132 (1983), Kimura-Kuroda et al., J. Gen Virol 67, 2663-2672 (1986), Zhang et al., J Med Virol 29, 133-138 (1989); and Roehrig et al., Virol 128, 118-126 (1983)) *JEV* HIAF and normal mouse serum were used as positive and negative antibody controls, respectively. Four *JEV*-specific, six *flavivirus*-subgroup specific, and two *flavivirus*-group reactive Mabs reacted similarly with the 4B clone or *JEV*-infected COS-1 cells (see Table 2).

TABLE 2

Characterization of proteins expressed by a pCDJE2-7 stably transformed clone (JE-4B) of COS-1 cells with JE virus-reactive antibodies.

| Mab or antiserum | Biological Activity of Mab: Specificity | Biological Function | Immunofluorescent intensity of cells: JEV infected | 4B |
|---|---|---|---|---|
| Mab: | | | | |
| MC3 | JEV Specific | | 2+ | 2+ |
| 2F2 | JEV Specific | HI, N | 4+ | 4+ |
| 112 | JEV Specific | | 4+ | 4+ |
| 503 | JEV Specific | N | 4+ | 3+ |
| 109 | Subgroup | HI | 2+ | 1+ |
| N 04 | Subgroup | HI, N | 3+ | 4+ |
| 201 | Subgroup | | 1+ | 1− |
| 203 | Subgroup | | 4+ | 3+ |
| 204 | Subgroup | | 2+ | 2+ |

TABLE 2-continued

Characterization of proteins expressed by a pCDJE2-7 stably transformed clone (JE-4B) of COS-1 cells with JE virus-reactive antibodies.

| Mab or antiserum | Biological Activity of Mab: Specificity | Biological Function | Immunofluorescent intensity of cells: JEV infected | 4B |
|---|---|---|---|---|
| 301 | Subgroup | HI | 2+ | 2+ |
| 504 | Flavivirus | | 4+ | 4+ |
| 6B6C-1 | Flavivirus | | 2+ | 2+ |
| 3B4C-4 | VEE | | — | — |
| H1AF: | | | | |
| Anti-JEV | | | 4+ | 3+ |
| Anti-WEE | | | — | — |
| PBS | | | — | — |

Example 4

Figure 4:
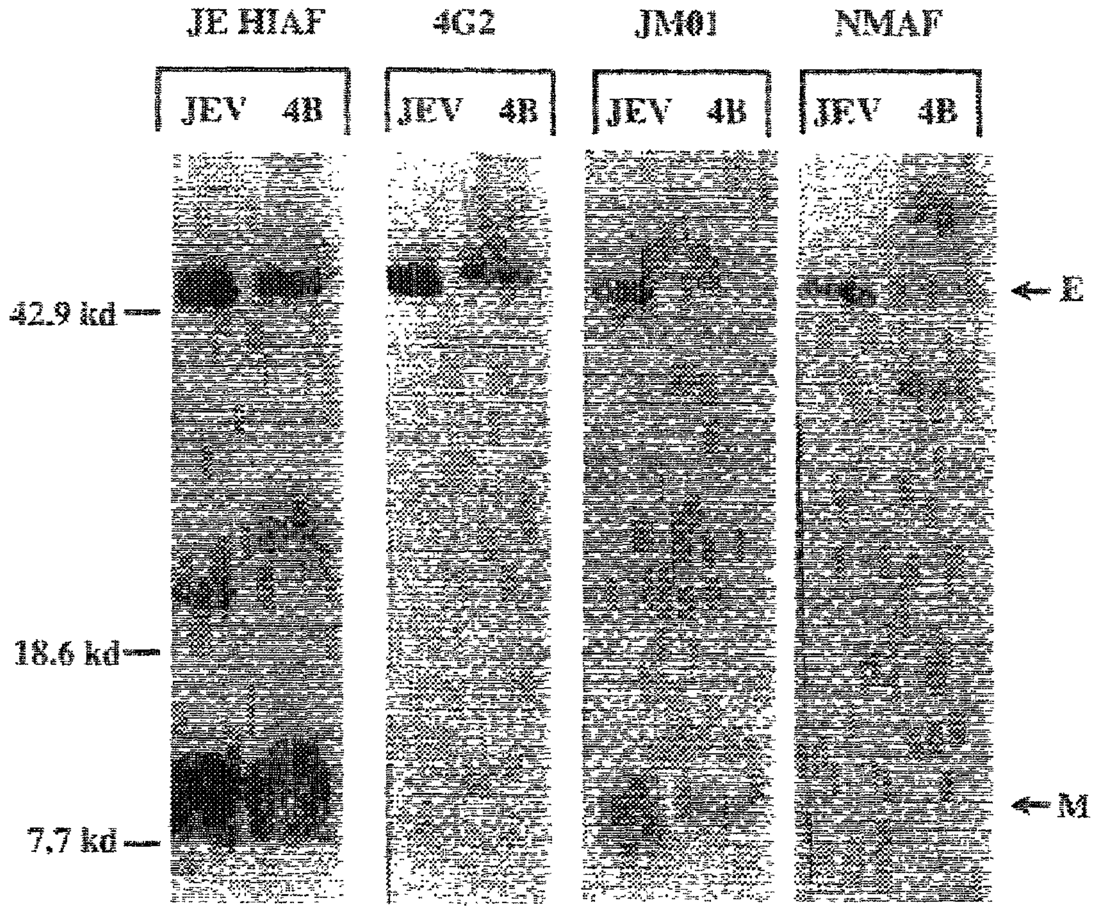
FIG. 4 shows SDS-PAGE-immunoblot analyses of the sucrose gradient purified subviral particles from JE-4B COS-1 culture fluid (4B, right lane of each pair) The density gradient purified JE virion from *JEV* infected C6/36 cell culture was used as a positive control (*JEV*, left lane of each pair) JE HIAF (hyperimmune ascetic fluid), 4G2, anti-E monoclonal antibody, JM01, anti-M monoclonal antibody, NMAF (normal mouse ascetic fluid)

Antigenic Properties and Immunological Detection of Subviral Particles Secreted by the JE-4B COS-1 Cell Line a. Preparation of subviral particles. JE-4B COS-1 cells were grown and maintained in medium containing 200 μg/mL of neomycin. The cultured medium was routinely harvested and stored at 4° C., and replenished twice weekly, and the cells were split 1:5 every 7-10 days Culture medium was clarified by centrifugation at 10,000 rpm for 30 min in a Sorvall F16/250 rotor at 4° C., and centrifuged further for 4 hr at 39,000 rpm in a Sorvall TH641 rotor at 4° C. through a 5% sucrose cushion (w/w, prepared with 10 mM Tris HCl, pH 7.5, 100 mM NaCl (TN buffer)) The pellet containing subviral particles was resuspended in TN buffer and stored at 4° C. Alternatively, 7% or 10% PEG-8000 (w/v) was added to the clarified culture medium The mixture was stirred at 4° C. for at least 2 hr, and the precipitated particles were collected by centrifugation at 10,000 rpm for 30 min. The precipitate was resuspended in TN buffer and stored at 4° C. The subviral particles were purified from both pelleted and PEG-precipitated preparations by rate zonal centrifugation in a 5-25% continuous sucrose gradient in TN at 38,000 rpm at 4° C. for 90 min. 1-mL fractions were collected from the top of the gradient, tested by antigen capture ELISA (see below), and the positive fractions loaded onto a 25-50% sucrose gradient in TN This was centrifuged overnight in an equilibrium density centrifugation at 35,000 rpm at 4° C. 0.9-mL fractions from the equilibrium gradients were collected from the bottom. They were tested by antigen-capture ELISA and assessed for hemagglutination (HA) activity at pH 6.6. An aliquot of 100 μL of each fraction was weighed precisely to determine its density. The ELISA-positive fractions were pooled and pelleted at 39,000 rpm at 4° C. for 3-4 hr and the pellet resuspended in TN buffer Antigen-capture ELISA and HA titers were determined on the pelleted samples. *JEV*-infected COS-1 cell supernatant was also subjected to similar purification protocols as detailed above and used as a positive control for the gradient analysis. JE virions were also purified from infected C6/36 cells 5-6 days postinfection by sedimentation in a glycerol/tartrate equilibrium gradient b. Western blots of subviral particles Gradient-purified samples of the subviral particles were mixed with electrophoresis sample buffer and run on 10 or 12.5% sodium dodecyl sulfate-containing polyacrylamide gels (SDS-PAGE) as described by Laemmli (Nature 277, 680-685 (1970)) Proteins were transferred to a nitrocellulose membrane and immunochemically detected with polyclonal *JEV* HIAF, *flavivirus* cross-reactive anti-E Mab 4G2 (Henchal et al., Amer. J Trop. Med Hyg 31, 830-836 (1982)), or mouse anti-prM peptide hyperimmune serum (JM01, Chiueh et al., unpublished results). FIG. 4 shows a comparison of the M and E proteins produced by *JEV* infected C6/36 and JE-4B COS-1 cells. Some nonspecific reactivity to E protein was observed in the normal mouse ascitic fluid and Jmo1 anti-peptide serum Proteins identical in size to M and E were secreted in the subviral particles and could be detected by E-specific Mab4G2 and prM-specific JM01 antiserum, respectively c. Density gradient detection of *JEV* subviral particles in culture medium. For ELISA, antigen-capture antibody (4G2) was diluted in 0.1 M sodium carbonate buffer, pH 9.6, and used to coat 96-well microtiter plates (Immulon II, Dynatech, Chantilly, Va.) by overnight incubation at 4° C. After blocking with 3% normal goat serum in PBS, two-fold serially-diluted samples were added to the 4G2-coated plate and incubated 1.5 hours at 37° C. Captured antigen was detected by horseradish peroxidase-conjugated 6B6C-1 Mag, and incubated for 1 hour at 37° C. The enzyme activity on the solid phase was then detected with TMB (3,3',5,5'-tetramethylbenzidine)-ELISA (Life Technologies, Grand Island, N.Y.).

Approximately 500 mL of cell culture medium from 15×150 $cm^2$ flasks of JE-4B cells was collected four days after cells were seeded PEG-precipitated subviral particles were resuspended in 2 mL of TN buffer, pH 7.5, a 0 7 mL aliquot of this resuspended pellet was loaded onto a 5-25% sucrose gradient Triton X-100, which disrupts subviral particles, was added to another 0.7 mL aliquot to a final concentration of 0.1% and this was loaded onto a 5-25% sucrose gradient prepared in TN buffer containing 0.1% Triton X-100. A definite opaque band was observed approximately 2.5 cm from the top of the gradient containing Triton X-100 but not in the gradient without detergent. Fractions (1 mL) were collected from top to bottom for each gradient and were analyzed by antigen capture ELISA (FIG. 5) Antigen was detected in fractions 4-6, indicating relatively rapid sedimentation characteristic of subviral particles Treatment of the PEG precipitate from JE-4B culture medium with Triton X-100 shifted the position of ELISA-reactive material to the top of the gradient. Thus treatment with Triton X-100 produces only slow-sedimenting molecules A similar finding was reported by Konishi et al., 1992 (Virol 188 714-720) These results show that rapidly sedimenting subviral particles containing prM/M and E could be disrupted by detergent treatment HA activity was determined in the pH range from 6.1 to 7.0 by the method of Clarke and Casals (Amer. J Trop Med Hyg. 7:561-573 (1958)). The subviral particle secreted by JE-4B cells and the virion particle produced by *JEV* infected COS-1 cells had a similar HA profile with the optimum pH determined to be 6.6

Example 5

Comparison of the Immune Response in Mice Vaccinated With pCDJE2-7 Nucleic Acid Vaccine of the Invention and Commercial *JEV* Vaccine Groups of five 3-week-old female, JCR outbred mice were injected intramuscularly in the left and right quadriceps with 100 μg of pCDJE2-7 plasmid in 100 μL of $dH_2O$ or were given doses of JE-VAX (manufactured by the Research Foundation for Microbial Disease of Osaka University and distributed by Connaught Laboratories, Swiftwater, Pa.) subcutaneously that are one-fifth the dose given to humans. The plasmid pCDNA3/CAT, which encodes and expresses an unrelated protein, (Invitrogen), was used as the negative vaccination control. Except for one group of pCDJE2-7-vaccinated mice, all animals were boosted 3 weeks later with an additional dose of plasmid or JE-VAX Mice were bled from the retroorbital sinus at 3, 6, 9, 23, 40 and 60 weeks after inoculation. *JEV* antibody titers were determined by enzyme-linked imunosorbent assay (ELISA) against purified *JEV* or by plaque reduction neutralization tests (PRNT) (Roehrig et al., Viro 171 49-60 (1989), and Hunt and Calisher, Amer J Trop Med Hyg 28 740-749 (1979))

The pCDJE2-7 nucleic acid vaccine and JE-VAX provided 100% seroconversion three weeks after the first vaccination in all three groups of mice (Table 3) The *JEV* ELISA and PRNT antibody titers reached the highest level at week 6 and week 9, respectively, after immunization. Mice receiving 1 dose of DNA vaccine had similar antibody responses as those receiving 2 doses. Comparable ELISA antibody titers were maintained in DNA-vaccinated groups up to 60 weeks, after which the experiment was terminated. However, only one of four mice in the JE-VAX group was *JEV* antibody positive at 60 weeks post-inoculation. The pCDNA3/CAT control group did not have nay measurable *JEV* antibody. These results demonstrate that a single dose of *JEV*-specific nucleic acid vaccine is more effective in maintaining *JEV* antibody in mice than the commercial, FDA approved JE-VAX vaccine

TABLE 3

Persistence of the immune response in mice immunized with pCDJE2-7 or JE-VEX vaccine.

| | ELISA Titer ($log_{10}$) | | | | | | $PRNT_{90\%}$ Titer | | |
|---|---|---|---|---|---|---|---|---|---|
| | 3 wks | 6 wks | 9 wks | 23 wks | 40 wks | 60 wks* | 3 wks | 6 wks | 9 wks |
| 1× pCDJE2-7 | 2.6-3.2 | 3.8-5.0 | 3.8-4.4 | >3.2 | >3.2 | 2.4, 2.4, 3.8, 4.4 | <20 | 20 | 40-160 |
| 2× pCDJE2-7 | 2.6-3.8 | 4.4 | 3.8-4.4 | >3.2 | >3.2 | 2.6, 3.8, 3.8 | <20 | 20-40 | 40-160 |

TABLE 3-continued

Persistence of the immune response in mice immunized with pCDJE2-7 or JE-VEX vaccine.

| | ELISA Titer ($log_{10}$) | | | | | | $PRNT_{90\%}$ Titer | | |
|---|---|---|---|---|---|---|---|---|---|
| | 3 wks | 6 wks | 9 wks | 23 wks | 40 wks | 60 wks* | 3 wks | 6 wks | 9 wks |
| 2× JE-VAX | 2.6-3.8 | 4.4-5.0 | 3.8-5.6 | >3.2 | >3.2 | <2, <2, <2, 4.4 | <20 | 20-40 | 20-160 |
| 2× pCDNA3/CAT | <2 | <2 | <2 | ND | ND | <2 | <20 | <20 | <20 |

Mice were inoculated with 1 or 2, 100 μg/dose plasmid DNA, or 1/5 human dose of JE-VAX vaccine Sera were collected for testing prior to the second immunization.
*Individual serum titers.

Example 6

Comparison of Various Nucleic Acid Vaccine Constructs of the Invention and Commercial *JEV* Vaccine for Effectiveness of Vaccination at Different Ages A similar level of *JEV* protein was expressed by COS-1 cells transformed by either pCDJE2-7 pCBJE1-14, or PCIBJES14. *JEV* antibody induction by these nucleic acid constructs was compared to JE-VAX commercial vaccine at two different ages at vaccination. Three-day (mixed sex) or 3-week-old (female) ICR outbred mice, 10 per group, were vaccinated intramuscularly with 50 or 100 μg of plasmid DNA, or subcutaneously with doses of JE-VAX that are one-tenth or one-fifth the dose given to humans. Serum specimens were collected at 3 and 7 weeks after immunization and tested at a 1.1600 dilution by ELISA using purified *JEV* as an antigen. Results are shown in Table 4

Plasmid pCBJE 1-14 provided the highest extent of seroconversion, i.e., antibody titer greater than 1 1600, achieving 80-100% at both ages of vaccination Administration of pCDJE2-7 or pCIBJES14 provided moderate seroconversion by 7 weeks when 3-day old mice were vaccinated (60% for each), but weaker seroconversion (40% and 10%, respectively) when measured 3 weeks after vaccination. When these plasmids were administered at the age of 3 weeks, however, seroconversions of 90% or 100% were attained at both 3 weeks and 7 weeks after vaccination. In contrast, the commercial vaccine, JE-VAX, conferred no seroconversion when administered at 3 days of age, and 100% when given at 3 weeks of age. Thus the nucleic acid TU's for *JEV* prM and E provided an extent of seroconversion better than a very high dose of the commercial vaccine, and unexpectedly high seroconversion in both young and more mature animals

TABLE 4

The age-dependent percent seropositive rate in mice following vaccination with various JEV vaccines.

| | 3-day old | | 3-week old | |
|---|---|---|---|---|
| | 3 weeks PV | 7 weeks PV | 3 weeks PV | 7 weeks PV |
| JE-VAX | 0 | 0 | 100 | 100 |
| pCDNA3/CAT | 0 | 0 | 0 | 0 |
| pCDJE2-7 | 40 | 60 | 90 | 90 |
| pC1BJES14 | 10 | 60 | 80 | 100 |
| pCBJE1-14 | 80 | 100 | 100 | 100 |

Example 7

Protective Immunity Conferred by the Nucleic Acid Vaccine of the Invention

Three-day old vaccinated groups from Example 6 were challenged 7 weeks after vaccination by intraperitoneal injection of 50,000 pfu/100 μL of the mouse-adapted *JEV* strain SA14 and observed for 3 weeks 100% protection was achieved in groups that received various nucleic acid TU-containing vaccine constructs for up to 21 days (Table 5) In contrast, 60% of the JE-VAX-vaccinated mice, as well as 70% of the pCDNA3/CAT-vaccinated negative controls, did not survive virus challenge by 21 days These results indicate that the nucleic acid TU's of the invention confer unexpectedly effective protection on vaccinated mice This suggests the possibility of employing the nucleic acid vaccine of the invention as an early childhood vaccine for humans. In contrast, JE-VAX, the inactivated human vaccine currently used, does not appear to be effective in young animals.

TABLE 5

Protection from JEV challenge in 8 week old mice following vaccination at 3 days old with various JEV vaccines.

| | Pre-challenge JEV | Days post-challenge survival rate (%) | | | | |
|---|---|---|---|---|---|---|
| Vaccine | seroconversion | 6 | 7 | 8 | 9 | 21 |
| JE-VAX | 0 | 100 | 100 | 60 | 40 | 40 |
| pCDNA3/CAT | 0 | 100 | 80 | 30 | 30 | 30 |
| pCDJE2-7 | 60 | 100 | 100 | 100 | 100 | 100 |
| pC1BJES14 | 60 | 100 | 100 | 100 | 100 | 100 |
| pCBJE1-14 | 100 | 100 | 100 | 100 | 100 | 100 |

Example 8

Passive Protection of Neonatal Mice Correlated with the Maternal Antibody Titer Female ICR mice at the age of 3 weeks were vaccinated with either one dose or two doses spaced two days apart of pCDJE2-7 plasmid DNA, at 100 μg/100 μL, or with two doses of JE-VAX that were one-fifth the dose given to humans. The negative control group received two doses of 100 μg/100 μL of pCDNA-3/CAT plasmid. Passive protection by maternal antibody was evaluated in pups resulting from matings of experimental females with non-immunized male mice that occurred nine weeks following the first vaccination or 6 weeks following the second vaccination Pups were challenged between 3-15 days after birth by intraperitoneal administration of 5,000 pfu/100 μL of mouse-adapted SA14 virus and observed daily for 3 weeks (see Table 6) The survival rates correlated with the maternal neutralizing antibody titers. 100% of pups nursed by mothers with a PRNT of 1.80 survived viral infection, whereas none of the pups from the control mother survived (Table 6) Partial protection of 45% and 75% was observed in older pups that were nursed by mothers with a PRNT titer of 1.20 and 1.40, respectively. The survival rates also correlated with the length of time that pups were nursed by the immune mother As just indicated, 13-15 day old pups had high survival rates None of the 3-4 day old pups, however, survived virus challenge when the mother had a PRNT titer of 1:20 or 1:40. Thus maternal antibody provides partial to complete protective immunity to the offspring. In addition, *JEV* antibody was detected by ELISA in the sera of 97% (29/30) of the post-challenge pups

TABLE 6

Evaluation of the ability of maternal antibody from JEV-nucleic acid-vaccinated female mice to protect their pups from fatal JEV encephalitis.

| Vaccinated mother | | JEV challenged pups | | |
|---|---|---|---|---|
| | | Challenge age | | |
| Vaccine | $PRNT_{90\%}$ | (days) | No. survival[1] | ELISA[2] |
| 1 × pCDJE2-7 | 40 | 4 | 0/11 | |
| 2× pCDJE2-7 | 80 | 4 | 12/12 | 12/12 |
| 2× JE-VAX | 20 | 3 | 0/16 | |
| 2× pCDNA-3/CAT | <10 | 5 | 0/14 | |
| 1× pCDJE2-7 | 20 | 15 | 5/11 | 5/5 |
| 2× pCDJE2-7 | 40 | 14 | 8/12 | 7/8 |
| 2× JE-VAX | 80 | 13 | 5/5 | 5/5 |
| 2× pCDNA-3/CAT | <10 | 14 | 0/14 | |

Mice were inoculated intramuscularly with 1 or 2. 100 μg dose of plasmid DNA. or subcutaneously with two. 1/5 human dose of JE-VAX vaccine Sera were collected 9 weeks post-vaccination for PRNT testing prior to mating with non-immune male

[1]No Survivors total for each litter

[2]Number of JEV ELISA-antibody-positive animals (titer ≧ 1:400)/No. of survivors. sera were collected for testing 12 weeks after challenge Example 9

Figure 6:
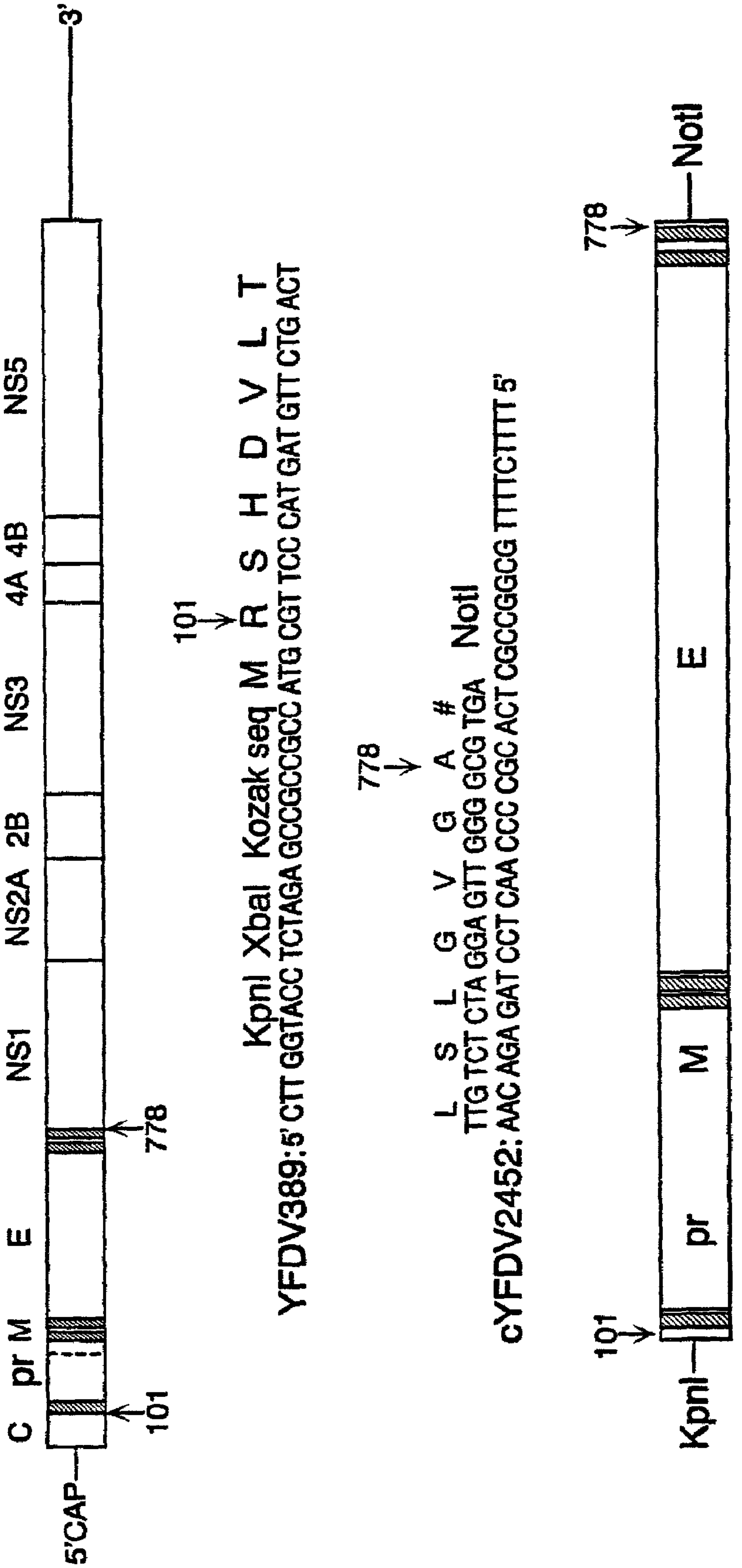
FIG. 6 is a map of the *yellow fever virus* (*YFV*) genome (top) and the DNA sequence of oligonucleotides (SEQ ID NOs: 8, 10, 11) (center) used in a reverse transcriptase-PCR to construct the transcription unit for the expression of *YFV* prM-E protein coding regions (bottom). Potential transmembrane domains of viral polyprotein are indicated by shaded areas. The amino acid sequences (SEQ ID NOs: 9 and 12) encoded by the oligonucleotides are also shown.
Figure 7:
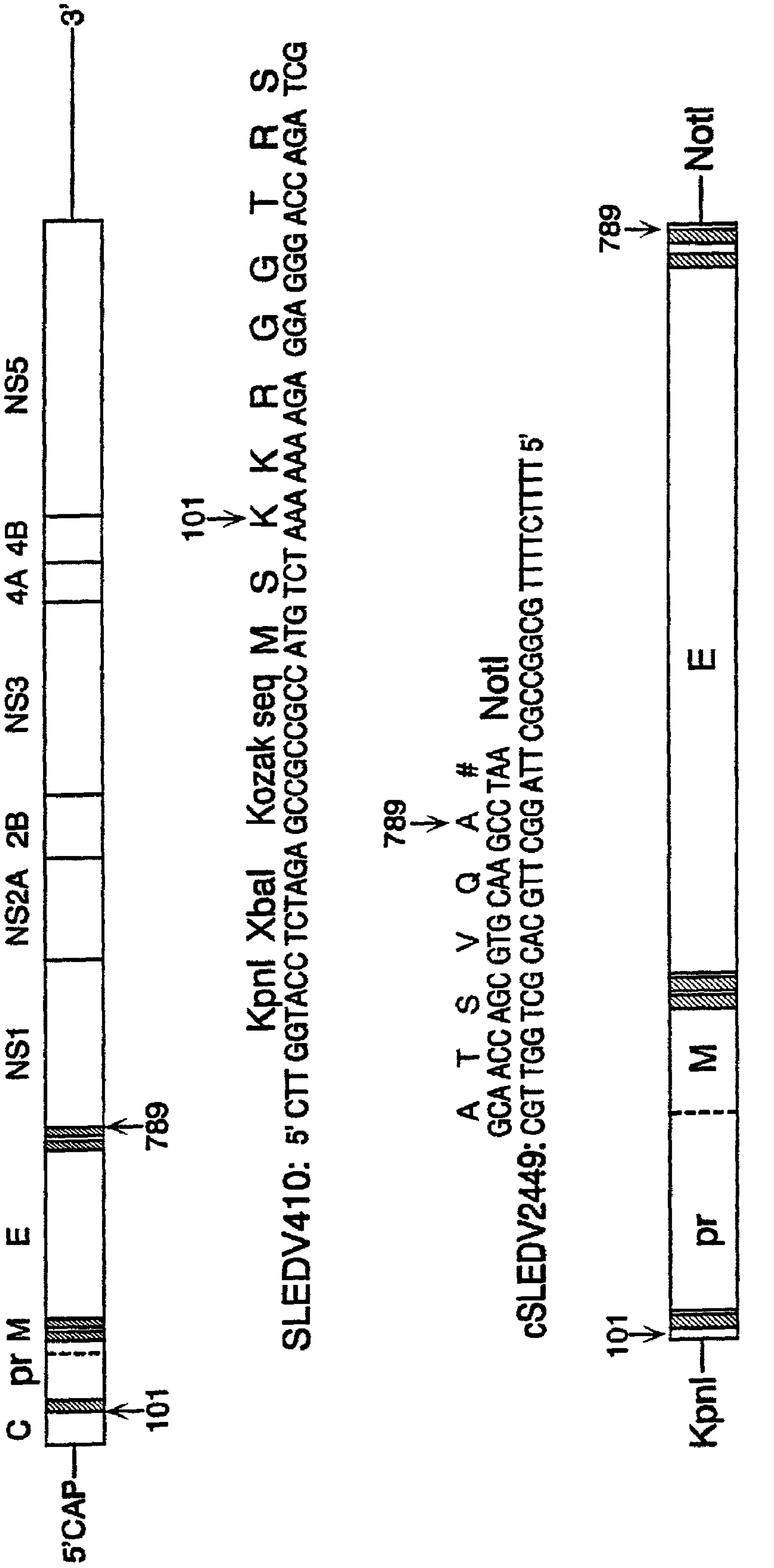
FIG. 7 is a map of the *St. Lous encephalitis virus* (*SLEV*) genome (top) and the DNA sequence of oligonucleotides (SEQ ID NOs: 13, 15, 16) (center) used in a reverse transcriptase-PCR to construct the transcription unit for the expression of *SLEV* prM-E protein coding regions (bottom). Potential transmembrane domains of viral polyprotein are indicated by shaded areas. The amino acid sequences (SEQ ID NOs: 14 and 17) encoded by the oligonucleotides are also shown.

Preparation of Recombinant Plasmids Containing Coding Sequences for *Yellow Fever Virus* (*YFV*) or *St. Louis Encephalitis Virus* (*SLEV*) prM and E Proteins A strategy similar to constructing the pCDJE2-7 recombinant plasmid was used to prepare *YFV* and *SLEV* recombinant plasmids. Genomic RNA was extracted from 150 μL of *YFV* strain TRI-788379 or SLE strain 78V-6507 virus seeds using QIAAM™ Viral RNA Kit (Qiagen, Santa Clarita, Calif.). The viral RNA was used as a template for amplification of *YFV* or *SLEV* prM and E gene coding regions. Primer sequences and structures of the amplified *YFV* and *SLEV* DNA products are shown in FIGS. 6 and 7, respectively. RT-PCR amplified cDNA, digested with KpnI and NotI enzymes, was inserted with the KpnI-NotI site of a eukaryotic expression plasmid vector, pCDNA3 (Invitrogen). Both strands of the cDNA were sequenced and verified for identity to sequences from *YFV* strain TRI-788379 or *SLEV* strain 78V-6507 (unpublished; Chang, 1998). Recombinant plasmids pCDYF2 and pCDSLE4-3, which contained the nucleotide sequences of the prM and E coding regions for *YFV* or *SLEV*, respectively, were purified using an ENDOFREE™ Plasmid Maxi Kit (Qiagen), and used for in vitro transformation or mouse immunization.

Figure 8:
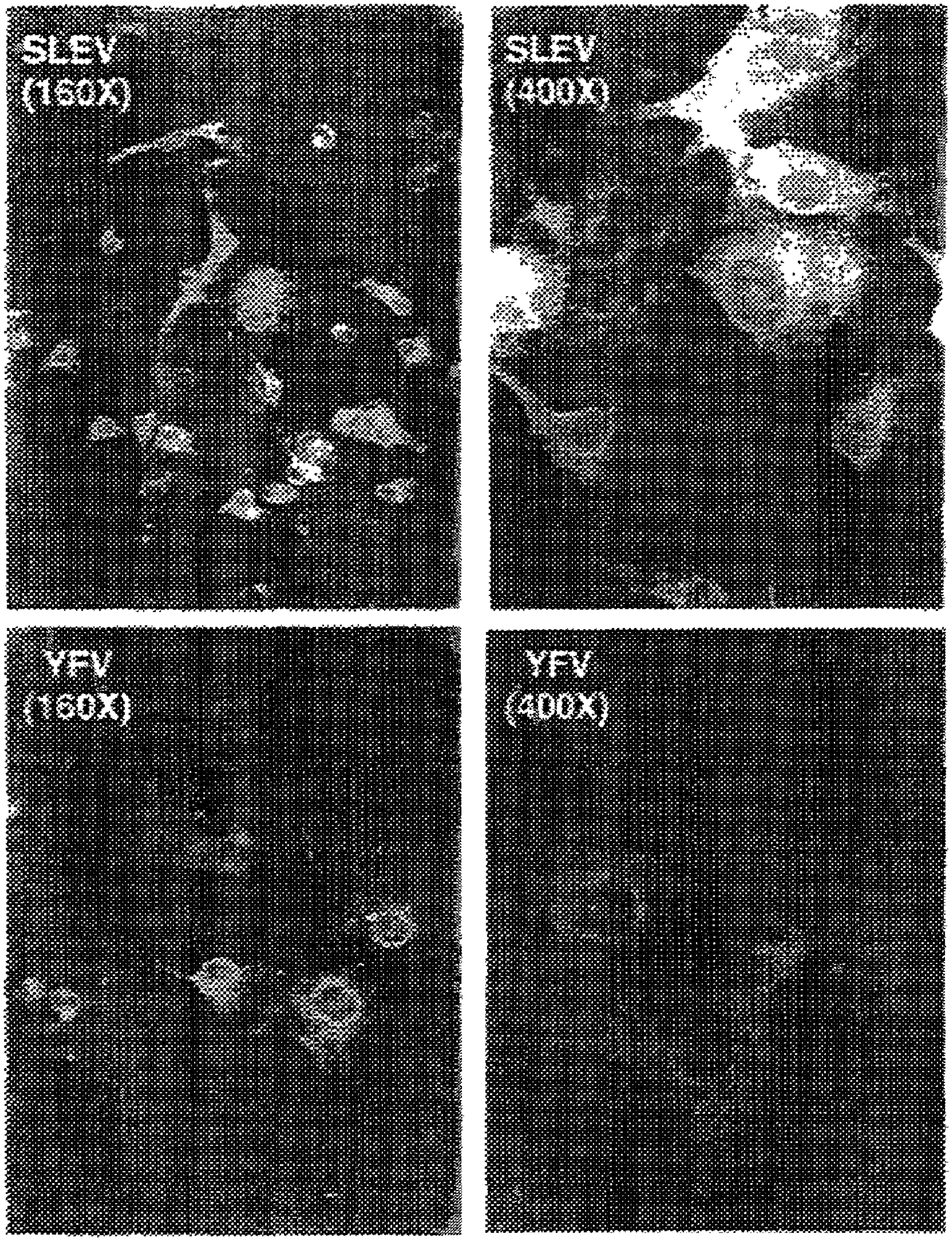
FIG. 8 shows photographs of YF or SLE viral proteins detected by an indirect immunofluorescent antibody assay (IFA) using either *YFV* or *SLEV* HIAF Viral proteins prM and E were expressed in COS-1 cells transformed by pCDYF2 or pCDSLE4-3, respectively

*YFV* or *SLEV* specific antigens were expressed in COS-1 cells transformed by pCDYF2 or pCDSLE4-3, respectively (FIG. 8). The level of expressed proteins was similar to a *YFV*- or *SLEV*-infected COS-1 cell control As in the *JEV* model, COS-1 cell lines transformed by vectors bearing genes for the viral antigens were obtained which constitutively express *YFV* or *SLEV* antigenic proteins Epitope mapping by IFA using a panel of *YFV* or *SLEV* E-specific Mabs indicated that the authentic E protein was expressed by the pCDYF2- or pCDSLE4-3-transformed COS-1 cells A preliminary study indicated that 100% of three week-old female, JCR mice servoconverted after intramuscular inoculation with a single dose of 100 μg/100 μL of pCDSLE4-3 plasmid in deionized water Example 10

Preparation of Plasmids Containing Coding Sequences for *Dengue Type* 2 Structural Proteins Procedures such as those carried out for *JEV* (see Example 1) are to be followed to prepare vectors including nucleic acid TU's for *dengue type* 2 antigens A plasmid containing the *dengue type* 2 gene region from prM to E is to be constructed. The *dengue type* 2 prM and E genes (Deubel et al., Virology 155:365-377 (1986); Gruenberg et al., J Gen. Virol 69 1301-1398 (1988), Hahn et al., Virology 162:167-180 (1988)) are to be ligated into a plasmid such as pCDNA3, and then excised and cloned into vectors such as pCBamp, pCEP4, pREP4, or pRc/RSV (supplied by Invitrogen, Carlsbad, Calif.) to enable expression. If necessary a *dengue type* 2 *virus*-specific sequence encoded in a cDNA sequence may be amplified using a procedure such as the polymerase chain reaction (PCR). Alternatively, if the viral RNA is the source of the gene region, a DNA sequence may be amplified by a reverse transcriptase-PCR procedure A DNA fragment including an initiation codon at the 5' end, and a termination codon at the 3' end is to be cloned into an expression vector at an appropriate restriction nuclease-specific site, in such a way that the cytomegalovirus (CMV) immediate early (IE) promoter, an initiation codon, and a terminator, are operably linked to the *dengue type* 2 *virus* sequence.

Example 11

Vaccination of Mice Using a *Dengue Type* 2 DNA Vaccine

The *dengue type* 2 nucleic TU vaccine encoding the gene region from prM to E prepared in Example 10 is to be suspended in a suitable pharmaceutical carrier, such as water for injection or buffered physiological saline, and injected intramuscularly into groups of weanling mice. Control groups receive a comparable plasmid preparation lacking the *dengue type* 2 specific genes The generation of *dengue type* 2-specific antibodies, and/or of *dengue type* 2-specific immune system cytotoxic cells, is to be assessed at fixed intervals thereafter, for example at weekly intervals At about two to four months after administration of the nucleic acid TU vaccine, mice are to be challenged with *dengue type* 2 *virus* Levels of viremia are to be assessed at appropriate intervals thereafter, such as every second day Passive protection by maternal antibody is to be assessed as indicated in Example 8.

I claim:

1. An isolated nucleic acid comprising a transcriptional unit for an immunogenic *flavivirus* antigen, wherein the transcriptional unit directs a host cell, after being incorporated therein, to synthesize the immunogenic antigen, and wherein the transcriptional unit comprises a prM signal sequence and a ribosomal binding sequence comprising GCCGCCGCC (positions 16 through 24 of SEQ ID NO: 1) located at position −9 to −1 relative to a start codon.

2. The nucleic acid of claim 1, wherein the *flavivirus* comprises *yellow fever virus, dengue serotype* 1*virus, dengue serotype* 2 *virus, dengue serotype* 3 *virus, dengue serotype* 4 *virus, St. Lous encephalitis virus, Japanese encephalitis virus*, or a mixture of two or more thereof.

3. The nucleic acid of claim 1, wherein the antigen is a prM/M protein, an E protein, or both a prM/M protein and an E protein.

4. The nucleic acid of claim 3, wherein the antigen is both the prM/M protein and the E protein and wherein the host cell secretes subviral particles comprising the prM/M protein and the E protein.

5. The nucleic acid of claim 1 which is DNA.

6. The nucleic acid of claim 1, wherein the transcriptional unit further comprises a control sequence disposed appropriately such that it operably controls synthesis of the antigen.

7. The nucleic acid of claim 6, wherein the control sequence is the cytomegalovirus immediate early promoter.

8. The nucleic acid of claim 1, wherein the transcriptional unit further comprises a poly-A terminator.

9. An isolated cell comprising the nucleic acid of claim 1.

10. The cell of claim 9, wherein the *flavivirus* comprises *yellow fever virus, dengue serotype* 1 *virus, dengue serotype* 2 *virus, dengue serotype* 3 *virus, dengue serotype* 4 *virus, St. Lous encephalitis virus, Japanese encephalitis virus*, or a mixture of two or more thereof.

11. The cell of claim 9, wherein the *flavivirus* antigen is a prM/M protein, an E protein, or both a prM/M protein and an E protein.

12. The cell of claim 11, wherein the antigen is both the prM/M protein and the E protein and wherein the cell secretes subviral particles comprising the prM/M protein and E protein.

13. A composition comprising the nucleic acid of claim 1 in a pharmaceutically acceptable carrier.

14. The composition of claim 13, wherein the *flavivirus* comprises *yellow fever virus, dengue serotype* 1 *virus, dengue serotype* 2 *virus, dengue serotype* 3 *virus, dengue serotype* 4 *virus, St. Lous encephalitis virus, Japanese encephalitis virus*, or a mixture of two or more thereof.

15. The composition of claim 13, wherein the antigen is a prM/M protein, an E protein, or both a prM/M protein and an E protein.

16. The composition of claim 15, wherein the antigen is both the prM/M protein and the E protein and wherein the cell secretes subviral particles comprising the prM/M protein and the E protein.

17. The composition of claim 13, wherein the nucleic acid is DNA.

18. The composition of claim 13, wherein the transcriptional unit further comprises a control sequence disposed appropriately such that it operably controls synthesis of the antigen.

19. The composition of claim 18, wherein the control sequence is the cytomegalovirus immediate early promoter.

20. The composition of claim 13, wherein the transcriptional unit further comprises a poly-A terminator.

21. The nucleic acid of claim 1, wherein the ribosomal binding sequence is located from positions −9 to +4 in the transcriptional unit, and consists of the sequence GCCGCCGCCATGG (positions 16 to 28 of SEQ ID NO: 1), GCCGCCGCCATGC (positions 16 to 28 of SEQ ID NO:3), or GCCGCCGCCATGT (positions 16 to 28 of SEQ ID NO: 13).

* * * * *

UNITED STATES PATENT AND TRADEMARK OFFICE

CERTIFICATE OF CORRECTION

PATENT NO. : 7,417,136 B1

APPLICATION NO. : 09/701536

DATED : August 26, 2008

INVENTOR(S) : Gwong-Jen J. Chang

It is certified that error appears in the above-identified patent and that said Letters Patent is hereby corrected as shown below:

On the title page, item [56]: In Other Publications:

On Page 1, under Lin *et al.*: "Elicitis" should read --Elicits--

On Page 1, under Wang *et al.*: "*Virology* 288:" should read --*Virology* 228--

On Page 3, Column 1, line 32: "$NS_1$" should read --NS1--

On Page 3, Column 1, line 33: "Overwriting" should read --Overwintering--

On Page 3, Column 2, line 22: "submit" should read --subunit--

Column 1, line 26: "*yellow fever virus. JEV,*" should read --*yellow fever virus*, *JEV,*--

Column 1, line 29: "others Altogether" should read --*others*. Altogether--

Column 1, line 30: "(1998))" should read --(1998)).--

Column 1, line 41: "virions M" should read --virions. M--

Column 1, line 62: "(1990))" should read --(1990)).--

Column 2, line 7: "(1985))" should read --(1985)).--

Column 2, line 13: "elderly; in" should read --elderly, in--

Column 2, line 39: "viremia" should read --viremia.--

Column 2, line 42: "(Tsai et al.) Whole" should read --(Tsai *et al.*). Whole--

Column 2, line 43: "do not have" should read --do have--

Column 2, line 44: "advantages The" should read --advantages. The--

Column 2, line 45: "host Such" should read --host. Such--

Column 2, line 46: "expensive Furthermore," should read --expensive. Furthermore,--

Column 2, line 54: "disease" should read --disease.--

Column 2, line 56: "WO 93/06214 The" should read --WO 93/06214. The--

Column 2, line 60: "*JEV*" should read --*JEV*.--

Column 2, line 63: "glycoprotien" should read --glycoprotein--

Column 3, line 3: "vaccine" should read --vaccine.--

Column 3, line 7: "*JEV* Recombinant" should read --*JEV*. Recombinant--

Column 3, line 13: "NS2B These" should read --NS2B. These--

Column 3, line 26: "(1992)) Dmitriev et al." should read --(1992)). Dmitiriev *et al.*--

Column 3, line 31: "fever Zhao" should read --fever. Zhao--

Column 3, line 49: "(1989)) Also" should read --(1989)). Also--

Column 3, line 61: "(1997)) Plasmid" should read --(1997)). Plasmid--

Column 3, line 63: "immunization In" should read --immunization. In--

Column 4, line 4: "(Kochel et al.) Challenge" should read --(Kochel *et al.*). Challenge)--

Column 4, line 23: "*YFV* Vaccine" should read --*YFV*. Vaccine--

Column 4, line 26: "alluded to" should read --alluded to.--

Column 4, line 33: "immunity There" should read --immunity. There--

Column 4, line 47: "*St. Lous*" should read --*St. Louis*--

Column 4, line 49: "(*JEV*) In important" should read --(*JEV*). In important--

Column 4, lines 50-51: "both In" should read --both. In--

Column 4, line 53: "antigens In" should read --antigens. In--

Column 5, lines 2-3: "anti-gens" should read --anti-gens.--

Column 5, line 11: "carrier In" should read --carrier. In--

Column 5, lines 13-14: "*JEV* Fur-thermore," should read --*JEV*. Fur-thermore,--

Column 5, line 25: "terminator" should read --terminator.--

Column 5, lines 52-53: "promoter Further-more," should read --promoter. Further-more,--

Column 5, line 66: "protecting" should read --protective--

Column 6, line 4: “inventory” should read --inventor--

Column 6, line 5: “acid is conferring” should read --acid in conferring--

Column 6, line 35: “PCIBamp” should read --pCIBamp--

Column 6, line 53: “pair) The” should read --pair). The--

Column 6, line 56: “ascetic” should read --ascitic--

Column 6, line 58: “ascetic fluid)” should read --ascitic fluid).--

Column 7, line 4: “*St. Lous*” should read --*St. Louis*--

Column 7, line 15: “HIAF Viral” should read --HIAF. Viral--

Column 7, line 17: “respectively” should read --respectively.--

Column 7, line 33: “molecules” should read --molecules.--

Column 7, line 45: “TU Although” should read --TU. Although--

Column 8, line 8: “TU In particular” should read --TU. In particular--

Column 8, line 10: “TU In particular” should read --TU. In particular--

Column 8, line 12: “cell In particular” should read --cell. In particular--

Column 8, line 31: “subject As” should read --subject. As--

Column 8, line 41: “organisms” should read --organisms.--

Column 8, line 45: “graph As” should read --graph. As--

Column 8, line 47: “TU The” should read --TU. The--

Column 8, line 63: “reference)” should read --reference).--

Column 9, line 1: “*St. Lous*” should read --*St. Louis*--

Column 9, line 4: “molecules They” should read --molecules. They--

Column 9, line 7: “agent Modifications” should read --agent. Modifications--

Column 9, line 11: “chemistry” should read --chemistry.--

Column 9, line 22: “DNA In” should read --DNA. In--

Column 9, line 26: “cell The” should read --cell. The--

Column 9, line 28: “virions” should read --virions.--

Column 9, line 29: “vivo or a” should read --vivo as a--

Column 9, line 39: “quarterly)) Since” should read --quarterly)). Since--

Column 9, line 42: “is mammalian cells Such” should read --in mammalian cells. Such--

Column 9, line 44: “operable” should read --operably--

Column 9, lines 44-45: “transla-tion In” should read --transla-tion. In--

Column 9, line 46: “promoter In” should read --promoter. In--

Column 9, line 60: “quarterly) The” should read --quarterly). The--

Column 9, line 62: “flavirridae” should read --flaviviridae--

Column 9, line 64: “(1990) The” should read --(1990). The--

Column 9, line 66: “scriptase From” should read --scriptase. From--

Column 10, line 2: “fragments Examples” should read --fragments. Examples--

Column 10, line 4: “(1991) Incorporation” should read --(1991). Incorporation--

Column 10, line 7: “engineering When” should read --engineering. When--

Column 10, line 8: “acid harboring” should read --acid molecule harboring--

Column 10, lines 9-10: “fragment Such” should read --fragment. Such--

Column 10, lines 12-13: “engineering Examples” should read --engineering. Examples--

Column 10, line 20: “obtained” should read --obtained.--

Column 10, line 35: “antigens A suitable” should read --antigens. A suitable--

Column 10, line 37: “acid In particular” should read --acid. In particular--

Column 10, line 40: “TU In” should read --TU. In--

Column 10, line 44: “functions When” should read --functions. When--

Column 10, line 49: “purposes” should read --purposes.--

Column 10, line 52: "particles These" should read --particles. These--

Column 10, line 56: "genone" should read --genome--

Column 10, line 60: "vaccine The" should read --vaccine. The--

Column 11, line 8: "limited b theory," should read --limited by theory,--

Column 11, line 12: "mechanisms" should read --mechanisms.--

Column 11, line 16: "antigens The" should read --antigens. The--

Column 11, lines 18-19: "anti-gens" should read --anti-gens.--

Column 11, line 23: "science They" should read --science. They--

Column 11, line 25: "Sciences) They" should read --Sciences). They--

Column 11, line 38: "administered One" should read --administered. One--

Column 11, line 43: "*degue,*" should read --*dengue,*--

Column 11, line 56: "100%" should read --100%.--

Column 11, line 59: "subject A significant" should read --subject. A significant--

Column 11, line 62: "invention Without" should read --invention. Without--

Column 11, line 64: "material" should read --maternal--

Column 11, line 67: "way" should read --way.--

Column 12, line 32: "Kpn1" should read --KpnI--

Column 12, line 36: "codone" should read --codon--

Column 12, line 43: "heater" should read --heated--

Column 12, line 58: "1989) RT-PCR" should read --1989). RT-PCR--

Column 12, line 59: "Kpn1" should read --KpnI--

Column 12, line 61: "(pCDNA2," should read --(pCDNA3,--

Column 13, line 7: "1990)" should read --1990).--

Column 13, line 13: "Nco1/Kpn1" should read --NcoI/KpnI--

Column 13, line 15: “pC1” should read --pCI--

Column 13, line 16: “Kpn1 The” should read --Kpn1. The--

Column 13, line 18: “fragment FIG. 3” should read --fragment. FIG. 3--

Column 13, line 19: “PCIBamp” should read --pCIBamp.--

Column 13, line 49: “(IFA) The” should read --(IFA). The--

Column 13, line 51: “positive For” should read --positive. For--

Column 14, lines 1-2: “per mL 10 μg” should read --per mL. 10 μg--

Column 14, line 6: “flask 48 h” should read --flask. 48 h--

Column 14, line 9: “serum 10 μL” should read --serum. 10 μL--

Column 14, line 10: “20 min IFA was” should read --20 min. IFA was--

Column 14, line 14: “H1AF” should read --HIAF--

Column 14, line 18: “pCDEJE2-7, pCEJE, or pRCJE” should read --pCDJE2-7, pCEJE, pREJE, or pRCJE--

Column 14, line 44: “sequence Following” should read --sequence. Following--

Column 14, line 47: “Table 1) This” should read --Table 1). This--

Column 14, line 51: “used Vectors” should read --used. Vectors--

Column 14, line 53: “analysis” should read --analysis.--

Column 14, line 61: “anitgen-positive” should read --antigen-positive--

Column 14, line 65: “pC1Bamp” should read --pCIBamp--

Column 14, line 65: “pC1BJES14” should read --pCIBJES14--

Column 15, line 15: “(negative control). pCDJE2-7.” should read --(negative control), pCDJE2-7,--

Column 15, line 16: “pC1BJES14, pCEJEm pREJE, or pRCJE, Cells” should read --pCIBJES14, pCEJE, pREJE. Cells--

Column 15, line 18: “cells The” should read --cells. The--

Column 15, line 28: “mg. mL,” should read --mg/mL,--

Column 15, line 29: “Neomycin-resistance” should read --Neomycin-resistant--

Column 15, line 31: “medium Expression” should read --medium. Expression--

Column 15, line 35: “neomycin” should read --neomycin.--

Column 15, line 42: “(1983)) *JEV*” should read --(1983)). *JEV*--

Column 15, line 64: “1-” should read --1+--

Column 16, line 33: “H1AF” should read --HIAF--

Column 16, line 49: “days Culture” should read --days. Culture--

Column 16, line 54: “(TN buffer)) The” should read --(TN buffer)). The--

Column 16, line 57: “medium The” should read --medium. The--

Column 16, line 67: “TN This” should read --TN. This--

Column 17, line 8: “buffer Antigen-capture” should read --buffer. Antigen-capture--

Column 17, line 14: “gradient” should read --gradient.--

Column 17, line 15: “particles Gradient” should read --particles. Gradient--

Column 17, line 19: “(1970)) Proteins” should read --(1970)). Proteins--

Column 17, lines 28-29: “serum Pro-teins” should read --serum. Pro-teins--

Column 17, line 31: “respectively” should read --respectively.--

Column 17, line 44: “seeded PEG-precipitated” should read --seeded. PEG-precipitated--

Column 17, line 46: “0 7 mL” should read --0.7 mL--

Column 17, line 47: “gradient Triton” should read --gradient. Triton--

Figure 5:
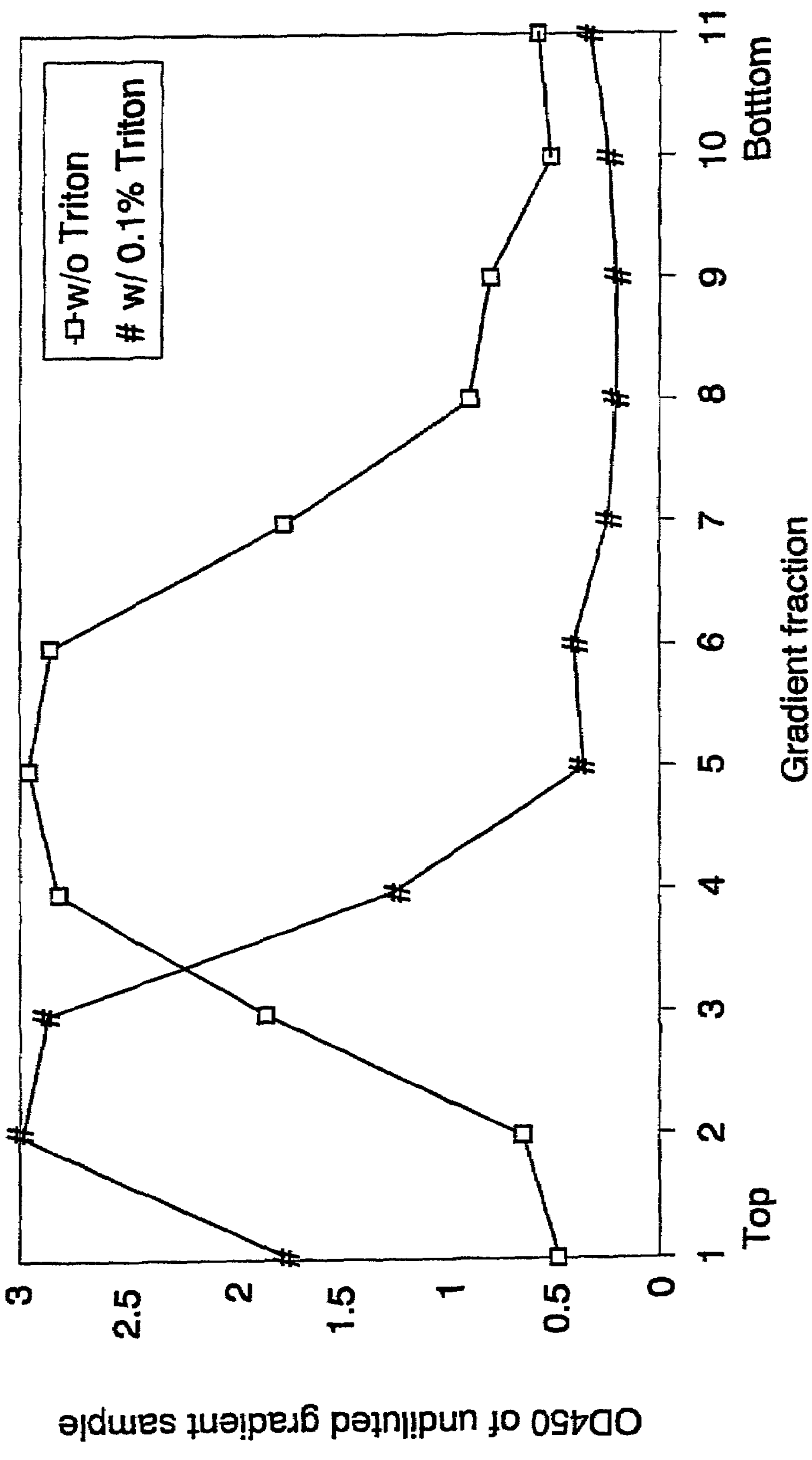
FIG. 5 shows a profile of the E antigen in a rate zonal sucrose gradient analysis prepared from the PEG precipitate of JE-4B cell culture medium with or without Triton X-100 treatment.

Column 18, line 1: “(FIG. 5) Antigen” should read --(FIG. 5). Antigen--

Column 18, line 3: “particles Treatment” should read --particles. Treatment--

Column 18, line 7: “molecules A similar” should read --molecules. A similar--

Column 18, line 8: “714-720)” should read --714-720).--

Column 18, line 11: “treatment” should read --treatment.--

Column 18, line 17: “to be 6.6” should read --to be 6.6.--

Column 18, line 23: “JCR” should read --ICR--

Column 18, line 34: “JE-VAX Mice” should read --JE-VAX. Mice--

Column 18, lines 36-37: “imunosorbent” should read --immunosorbent--

Column 18, line 40: “(1979))” should read --(1979)).--

Column 18, line 43: “(Table 3) The” should read --(Table 3). The--

Column 18, line 51: “nay” should read --any--

Column 18, line 54: “vaccine” should read --vaccine.--

Column 18, line 58: “JE-VEX” should read --JE-VAX--

Column 19, line 3: “JE-VEX” should read --JE-VAX--

Column 19, line 12: “vaccine Sera” should read --vaccine. Sera--

Column 19, line 23: “PCIBJES14” should read --pCIBJES14--

Column 19, line 30: “1.1600” should read --1:1600--

Column 19, line 31: “Table 4” should read --Table 4.--

Column 19, line 33: “1 1600” should read --1:1600--

Column 19, line 34: “vaccination Administration” should read --vaccination. Administration--

Column 19, line 46: “animals” should read --animals.--

Column 19, line 57: “pC1BJES14” should read --pCIBJES14--

Column 19, line 67: “3 weeks 100%” should read --3 weeks. 100%--

Column 20, line 16: “(Table 5) In” should read --(Table 5). In--

Column 20, line 19: “days These” should read --days. These--

Column 20, line 21: “mice This” should read --mice. This--

Column 20, line 50: “vaccination Pups” should read --vaccination. Pups--

Column 20, line 53: “6) The” should read --6). The--

Column 20, line 55: "1.80" should read --1:80--

Column 20, line 57: "6) Partial" should read --6). Partial--

Column 20, line 59: "1.20 and 1.40," should read --1:20 and 1:40,--

Column 20, line 61: "mother As" should read --mother. As--

Column 20, line 62: "rates None" should read --rates. None--

Column 20, line 67: "pups" should read --pups.--

Column 21, line 20: "2. 100 µg" should read --2 100 µg--

Column 21, line 21: "DNA. or subcutaneously with two. 1/5 human dose of JE-VAX vaccine Sera" should read --DNA or subcutaneously with two 1/5 human dose of JE-VAX vaccine. Sera--

Column 21, line 23: "non-immune male" should read --non-immune male.--

Column 21, line 24: "No Survivors total for" should read --No. Survivors/total--

Column 21, line 36: "QIAAM" should read --QIAAMP--

Column 21, lines 42-43: "inserted with the" should read --inserted into the--

Column 21, line 54: "control As" should read --control. As--

Column 22, line 3: "proteins Epitope" should read --proteins. Epitope--

Column 22, line 6: "cells A" should read --cells. A--

Column 22, line 7: "JCR" should read --ICR--

Column 22, line 8: "servoconverted" should read --seroconverted--

Column 22, line 10: "water" should read --water.--

Column 22, line 16: "antigens" should read --antigens.--

Column 22, line 29: "procedure A" should read --procedure. A--

Column 22, line 46: "genes The" should read --genes. The--

Column 22, line 49: "intervals At" should read --intervals. At--

Column 22, line 52: "*virus* Levels" should read --*virus*. Levels--

Column 22, line 54: "day Passive" should read --day. Passive--

Column 29, line 28: "1virus" should read --1 virus--

Column 29, line 30: "*St. Lous*" should read --*St. Louis*--

Column 29, lines 49-50: "*St. Lous*" should read --*St. Louis*--

Column 30, line 28: "*St. Lous*" should read --*St. Louis*--

Signed and Sealed this

Nineteenth Day of January, 2010

David J. Kappos
*Director of the United States Patent and Trademark Office*